US012471910B2

(12) United States Patent
Wales et al.

(10) Patent No.: US 12,471,910 B2
(45) Date of Patent: Nov. 18, 2025

(54) SUTURE BASED CLOSURE DEVICE FOR USE WITH ENDOSCOPE

(71) Applicant: BOSTON SCIENTIFIC SCIMED, INC., Maple Grove, MN (US)

(72) Inventors: Ryan V. Wales, Northborough, MA (US); Paul J. Smith, Smithfield, RI (US); Scott E. Brechbiel, Burlington, MA (US); Kevin L. Bagley, Natick, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 9 days.

(21) Appl. No.: 18/378,962

(22) Filed: Oct. 11, 2023

(65) Prior Publication Data

US 2024/0032909 A1 Feb. 1, 2024

Related U.S. Application Data

(63) Continuation of application No. 17/170,522, filed on Feb. 8, 2021, now Pat. No. 11,812,944.

(Continued)

(51) Int. Cl.
*A61B 17/04* (2006.01)

(52) U.S. Cl.
CPC ...... *A61B 17/0469* (2013.01); *A61B 17/0493* (2013.01)

(58) Field of Classification Search
CPC ............ A61B 17/0469; A61B 17/0493; A61B 17/06066; A61B 1/00137; A61B 1/00101; A61B 1/00087
See application file for complete search history.

(56) References Cited

U.S. PATENT DOCUMENTS 4,436,087 A 3/1984 Ouchi
4,911,148 A * 3/1990 Sosnowski ......... A61B 1/00165 600/164

(Continued)

FOREIGN PATENT DOCUMENTS

CA 2682488 A1 10/2008
DE 202005022017 U1 5/2012

(Continued)

OTHER PUBLICATIONS

International Search Report and Written Opinion dated Aug. 20, 2019 for International Application No. PCT/US2019/033748.

(Continued)

*Primary Examiner* — Tuan V Nguyen
(74) *Attorney, Agent, or Firm* — Seager, Tufte & Wickhem, LLP

(57) ABSTRACT

A suture device for use in combination with a delivery system including a lumen extending through the delivery system includes a needle usable to carry a suture, a distal shuttle configured to releasably secure the needle, a sleeve disposable over the distal shuttle, the distal shuttle movable relative to the sleeve between a locked position in which the needle is locked to the distal shuttle and an unlocked position in which the needle is releasable from the distal shuttle. The suture device includes a distal assembly including an elongate tool guide movable between a deployment configuration in which the elongate tool guide is substantially parallel with the distal assembly and a working configuration in which the elongate tool guide curves away from the distal assembly.

20 Claims, 35 Drawing Sheets

Related U.S. Application Data

(60) Provisional application No. 62/978,029, filed on Feb. 18, 2020.

(56) References Cited

U.S. PATENT DOCUMENTS

| | | | |
|---|---|---|---|
| 5,478,344 A | 12/1995 | Stone | |
| 5,584,861 A | 12/1996 | Swain et al. | |
| 6,086,608 A | 7/2000 | Ek et al. | |
| 6,200,329 B1 | 3/2001 | Fung et al. | |
| 6,494,888 B1 | 12/2002 | Laufer et al. | |
| 6,506,196 B1 | 1/2003 | Laufer | |
| 6,554,845 B1 | 4/2003 | Fleenor et al. | |
| 6,569,085 B2 | 5/2003 | Kortenbach et al. | |
| 6,626,917 B1 | 9/2003 | Craig | |
| 6,663,639 B1 | 12/2003 | Laufer et al. | |
| 6,719,763 B2 | 4/2004 | Chung et al. | |
| 6,740,030 B2 | 5/2004 | Martone et al. | |
| 6,746,457 B2 | 6/2004 | Dana et al. | |
| 6,755,843 B2 | 6/2004 | Chung et al. | |
| 6,773,441 B1 | 8/2004 | Laufer et al. | |
| 6,808,491 B2 | 10/2004 | Kortenbach et al. | |
| 6,821,285 B2 | 11/2004 | Laufer et al. | |
| 6,835,200 B2 | 12/2004 | Laufer et al. | |
| 6,908,427 B2 | 6/2005 | Fleener et al. | |
| 6,997,931 B2 | 2/2006 | Sauer et al. | |
| 7,056,284 B2 | 6/2006 | Martone et al. | |
| 7,063,710 B2 | 6/2006 | Takamoto et al. | |
| 7,063,715 B2 | 6/2006 | Onuki et al. | |
| 7,094,246 B2 | 8/2006 | Anderson et al. | |
| 7,144,401 B2 | 12/2006 | Yamamoto et al. | |
| 7,147,646 B2 | 12/2006 | Dana et al. | |
| 7,153,314 B2 | 12/2006 | Laufer et al. | |
| 7,220,266 B2 | 5/2007 | Gambale | |
| 7,232,445 B2 | 6/2007 | Kortenbach et al. | |
| 7,235,086 B2 | 6/2007 | Sauer et al. | |
| 7,326,221 B2 | 2/2008 | Sakamoto et al. | |
| 7,344,545 B2 | 3/2008 | Takemoto et al. | |
| 7,347,863 B2 | 3/2008 | Rothe et al. | |
| 7,361,180 B2 | 4/2008 | Saadat et al. | |
| 7,530,985 B2 | 5/2009 | Takemoto et al. | |
| 7,601,161 B1 | 10/2009 | Nobles et al. | |
| 7,618,425 B2 | 11/2009 | Yamamoto et al. | |
| 7,713,277 B2 | 5/2010 | Laufer et al. | |
| 7,722,633 B2 | 5/2010 | Laufer et al. | |
| 7,727,246 B2 | 6/2010 | Sixto, Jr. et al. | |
| 7,736,373 B2 | 6/2010 | Laufer et al. | |
| 7,776,057 B2 | 8/2010 | Laufer et al. | |
| 7,776,066 B2 | 8/2010 | Onuki et al. | |
| 7,842,051 B2 | 11/2010 | Dana et al. | |
| 7,846,180 B2 | 12/2010 | Cerier | |
| 7,857,823 B2 | 12/2010 | Laufer et al. | |
| 7,896,893 B2 | 3/2011 | Laufer et al. | |
| 7,918,867 B2 | 4/2011 | Dana et al. | |
| 7,951,157 B2 | 5/2011 | Gambale | |
| 7,992,571 B2 | 8/2011 | Gross et al. | |
| 7,993,368 B2 | 8/2011 | Gambale et al. | |
| 8,016,840 B2 | 9/2011 | Takemoto et al. | |
| 8,021,376 B2 | 9/2011 | Takemoto et al. | |
| 8,057,494 B2 | 11/2011 | Laufer et al. | |
| 8,062,314 B2 | 11/2011 | Sixto, Jr. et al. | |
| 8,066,721 B2 | 11/2011 | Kortenbach et al. | |
| 8,105,355 B2 | 1/2012 | Page et al. | |
| 8,211,123 B2 | 7/2012 | Gross et al. | |
| 8,216,253 B2 | 7/2012 | Saadat et al. | |
| 8,226,667 B2 | 7/2012 | Viola et al. | |
| 8,277,468 B2 | 10/2012 | Laufer et al. | |
| 8,287,554 B2 | 10/2012 | Cerier et al. | |
| 8,287,556 B2 | 10/2012 | Gilkey et al. | |
| 8,308,765 B2 | 11/2012 | Saadat et al. | |
| 8,313,496 B2 | 11/2012 | Sauer et al. | |
| 8,361,089 B2 | 1/2013 | Chu | |
| 8,388,632 B2 | 3/2013 | Gambale | |
| 8,425,555 B2 | 4/2013 | Page et al. | |
| 8,454,631 B2 | 6/2013 | Viola et al. | |
| 8,480,691 B2 | 7/2013 | Dana et al. | |
| 8,540,735 B2 | 9/2013 | Mitelberg et al. | |
| 8,551,120 B2 | 10/2013 | Gambale | |
| 8,585,720 B2 | 11/2013 | Gross et al. | |
| 8,632,553 B2 | 1/2014 | Sakamoto et al. | |
| 8,679,136 B2 | 3/2014 | Mitelberg | |
| 8,709,022 B2 | 4/2014 | Stone et al. | |
| 8,764,771 B2 | 7/2014 | Chu | |
| 8,882,785 B2 | 11/2014 | DiCesare et al. | |
| 8,926,634 B2 | 1/2015 | Rothe et al. | |
| 8,992,570 B2 | 3/2015 | Gambale et al. | |
| 9,011,466 B2 | 4/2015 | Adams et al. | |
| 9,089,325 B2 | 7/2015 | Mitelberg et al. | |
| 9,125,646 B2 | 9/2015 | Woodard, Jr. et al. | |
| 9,198,562 B2 | 12/2015 | Mitelberg et al. | |
| 9,320,515 B2 | 4/2016 | Dana et al. | |
| 9,486,126 B2 | 11/2016 | West et al. | |
| 9,504,465 B2 | 11/2016 | Chu | |
| 9,510,817 B2 | 12/2016 | Saadat et al. | |
| 9,549,728 B2 | 1/2017 | Chu | |
| 9,750,494 B2 | 9/2017 | Gross et al. | |
| 9,788,831 B2 | 10/2017 | Mitelberg | |
| 9,844,366 B2 | 12/2017 | Woodard, Jr. et al. | |
| 9,867,610 B2 | 1/2018 | Mitelberg et al. | |
| 10,045,871 B2 | 8/2018 | Saadat et al. | |
| 10,143,463 B2 | 12/2018 | Dana et al. | |
| 10,194,902 B2 | 2/2019 | Nobles et al. | |
| 10,335,142 B2 | 7/2019 | Raybin et al. | |
| 2002/0107530 A1 | 8/2002 | Sauer et al. | |
| 2002/0142119 A1 | 10/2002 | Seward et al. | |
| 2002/0165534 A1* | 11/2002 | Hayzelden | A61M 25/0144 604/95.04 |
| 2003/0204205 A1 | 10/2003 | Sauer et al. | |
| 2004/0002699 A1 | 1/2004 | Ryan et al. | |
| 2004/0138706 A1 | 7/2004 | Abrams et al. | |
| 2005/0033319 A1 | 2/2005 | Gambale et al. | |
| 2005/0250985 A1 | 11/2005 | Saadat et al. | |
| 2005/0251177 A1 | 11/2005 | Saadat et al. | |
| 2006/0282094 A1 | 12/2006 | Stokes et al. | |
| 2007/0270908 A1 | 11/2007 | Stokes et al. | |
| 2008/0086148 A1 | 4/2008 | Baker et al. | |
| 2009/0177031 A1 | 7/2009 | Surti et al. | |
| 2009/0287188 A1* | 11/2009 | Golden | A61M 25/0147 604/528 |
| 2010/0137681 A1 | 6/2010 | Ewers et al. | |
| 2010/0198006 A1 | 8/2010 | Greenburg et al. | |
| 2012/0158023 A1 | 6/2012 | Miltelberg et al. | |
| 2012/0271327 A1 | 10/2012 | West et al. | |
| 2013/0096581 A1 | 4/2013 | Gilkey et al. | |
| 2013/0304093 A1 | 11/2013 | Serina et al. | |
| 2014/0121457 A1 | 5/2014 | Mort et al. | |
| 2014/0128668 A1 | 5/2014 | Cox et al. | |
| 2015/0126983 A1 | 5/2015 | Alvarado et al. | |
| 2016/0045197 A1 | 2/2016 | Mitelberg et al. | |
| 2016/0235400 A1 | 8/2016 | Hiernaux et al. | |
| 2017/0042534 A1 | 2/2017 | Nobles et al. | |
| 2017/0086817 A1 | 3/2017 | Mitelberg | |
| 2017/0086818 A1 | 3/2017 | Mitelberg | |
| 2017/0119371 A1 | 5/2017 | Mims et al. | |
| 2017/0319197 A1 | 11/2017 | Gross et al. | |
| 2018/0042602 A1 | 2/2018 | Mitelberg et al. | |
| 2018/0042603 A1 | 2/2018 | Mitelberg et al. | |
| 2018/0153381 A1 | 6/2018 | Wei et al. | |
| 2018/0221009 A1 | 8/2018 | Mitelberg et al. | |
| 2018/0235604 A1 | 8/2018 | Comee et al. | |
| 2018/0344501 A1 | 12/2018 | Saadat et al. | |

FOREIGN PATENT DOCUMENTS

| | | | |
|---|---|---|---|
| EP | 1520509 A1 | 4/2005 | |
| EP | 2108304 A2 | 10/2009 | |
| JP | H05115426 A | 5/1993 | |
| JP | 2010505524 A | 2/2010 | |
| JP | 2013052258 A | 3/2013 | |
| JP | 2016538010 A | 12/2016 | |
| WO | 0189393 A1 | 11/2001 | |
| WO | 2008016592 A2 | 2/2008 | |
| WO | 2008045376 A2 | 4/2008 | |
| WO | 2008098124 A1 | 8/2008 | |
| WO | 2010036227 A1 | 4/2010 | |

(56) References Cited

FOREIGN PATENT DOCUMENTS

| | | | |
|---|---|---|---|
| WO | 2016200811 | A1 | 12/2016 |
| WO | 2017087856 | A1 | 5/2017 |
| WO | 2018156603 | A1 | 8/2018 |

OTHER PUBLICATIONS

International Search Report and Written Opinion dated Oct. 1, 2019 for International Application No. PCT/US2019/038006.

Invitation to Pay Additional Fees dated Sep. 26, 2019 for International Application No. PCT/US2019/037995.

International Search Report and Written Opinion dated Dec. 6, 2019 for International Application No. PCT/US2019/037995.

International Search Report and Written Opinion dated Nov. 18, 2019 for International Application No. PCT/US2019/049774.

International Search Report and Written Opinion dated Sep. 20, 2019 for International Application No. PCT/US2019/039312.

International Search Report and Written Opinion dated May 31, 2021 for International Application No. PCT/US2021/017106.

* cited by examiner

SUTURE BASED CLOSURE DEVICE FOR USE WITH ENDOSCOPE

CROSS REFERENCE TO RELATED APPLICATIONS

This application is a continuation of U.S. patent application Ser. No. 17/170,522, filed Feb. 8, 2021, which claims the benefit of U.S. Provisional Patent Application Ser. No. 62/978,029 filed on Feb. 18, 2020, the disclosure of which is incorporated herein by reference.

TECHNICAL FIELD

The disclosure is directed to devices for suturing tissue and more particularly to devices that work with an endoscope or similar device for endoscopically suturing tissue.

BACKGROUND

A variety of endoscopic treatments may result in defects (or wounds) that are too large for known closure methods. Examples of such endoscopic treatments include removal of large lesions, tunneling under the mucosal layer, full thickness removal of tissue, treating other organs by passing outside of the gastrointestinal tract, and post-surgical repairs such as post-surgical leaks. Endoscopic treatments also include bariatric revision procedures. Of the known devices and methods for endoscopically closing large defects, each has certain advantages and disadvantages.

SUMMARY

The disclosure is directed to several alternative designs, materials and methods of devices for endoscopically closing large defects. An example is a suture device for use in combination with a delivery system including a lumen extending through the delivery system. The suture device includes a suture translation assembly that is configured to be axially translatable within the lumen of the delivery system and that includes a distal end. A guide member is configured to permit the suture translation assembly to extend through the guide member and to translate relative to the guide member and an elongate tool guide having a distal end is disposed relative to the distal assembly, the elongate tool guide movable between a deployment configuration in which the elongate tool guide is substantially parallel with the distal assembly and a working configuration in which the elongate tool guide curves away from the distal assembly.

Alternatively or additionally, the distal assembly may define a working area between the guide member and the endcap, and when the elongate tool guide is in its working configuration, the elongate tool guide may be positioned to guide a tool extended through the elongate tool guide into the working area.

Alternatively or additionally, the elongate tool guide may include a guide structure that is fixedly secured to the distal assembly and a polymeric tubular member that is secured to the guide structure and extends proximally therefrom.

Alternatively or additionally, the elongate tool guide may move from its deployment configuration into its working configuration in response to a tool being extended distally through the elongate tool guide.

Alternatively or additionally, the polymeric tubular member is in a collapsed configuration when the elongate tool guide is in its deployment configuration.

Alternatively or additionally, the polymeric tubular member is in an expanded configuration when the elongate tool guide is in its working configuration.

Alternatively or additionally, the elongate tool guide may include a guide structure that is pivotably secured to the distal assembly and a polymeric tubular member that is secured to the guide structure and extends proximally therefrom, the guide structure and the polymeric tubular member together defining a lumen. The elongate tool guide may include a pivot structure that protrudes into the lumen such that a tool being extended distally through the elongate tool guide will contact the pivot structure, where further distal urging of the tool will cause the tool to interact with the pivot structure and cause the guide structure to pivot relative to the distal assembly, thereby moving the elongate tool guide from its deployment configuration into its working configuration.

Alternatively or additionally, the elongate tool guide may include an elongate structure defining at least a first lumen and a second lumen, where the first lumen may be configured to accommodate a tool extending therethrough. A metallic ribbon may extend through the second lumen and may be movable between a linear configuration in which the metallic ribbon is straight and a remembered configuration in which the metallic ribbon is curved. The elongate structure may be straight when the metallic ribbon is straight and the elongate structure may be curved when the metallic ribbon is curved.

Alternatively or additionally, the elongate tool guide may include an elongate structure defining at least a first lumen and a second lumen, where the first lumen may be configured to accommodate a tool extending therethrough. An elongate bi-stable member may extend through the second lumen and may be member movable between a stable configuration in which the elongate bi-stable member is straight and an unstable configuration in which the metallic ribbon is curved. The elongate structure may be straight when the bi-stable metal element is straight and the elongate structure may be curved when the bi-stable metal element is curved.

Alternatively or additionally, the elongate tool guide may include a plurality of conduit segments that are joined together via living hinges formed between adjacent conduit segments of the plurality of conduit segments, each of the plurality of conduit segments including at least one control aperture extending through each conduit segment and at least one control cable extending through each of the at least one control aperture of each conduit segment. Applying an axial force to the at least one control cable may cause the elongate tool guide to move between its deployment configuration and its working configuration.

Alternatively or additionally, the suture translation assembly may include a needle that is usable to carry a suture, a distal shuttle that is configured to releasably secure the needle and a user interface that extends proximally from the distal shuttle and is configured to enable a user to releasably secure the needle.

Alternatively or additionally, the suture device may further include a distal assembly that is configured to be securable to the distal end of the delivery system and that includes an endcap configured to releasably engage and disengage the needle, the endcap configured to engage the needle when the needle is advanced distally into the endcap, and to release the needle when the needle is locked to the distal shuttle and the distal shuttle is withdrawn proximally.

Alternatively or additionally, the endcap may include a proximal needle opening that is configured to accommodate the needle when the needle is advanced distally into the endcap, and that aligns with a longitudinal axis of the needle, one or more securement openings that are arranged orthogonal to the proximal needle opening and one or more securements that are disposed within the securement openings, the one or more securements configured to releasably engage the distal detent of the needle.

Alternatively or additionally, moving the translating handle distally from a neutral position may cause the member to move to the locked position and moving the translating handle proximally from the neutral position may cause the member to move to the unlocked position.

Alternatively or additionally, the delivery system may include an endoscope and the lumen may include a working channel of the endoscope.

Another example is a suture device for use in combination with an endoscope having a working channel and a distal end. The suture device includes a translation assembly that is configured to be axially translatable within the working channel and that includes a needle that is configured to carry a suture, a distal shuttle that is configured to releasably secure the needle and a sleeve that is disposable over the distal shuttle and sleeve movable between a locked position in which the needle is secured to the distal shuttle and an unlocked position in which the needle is releasable from the distal shuttle. The suture device includes a distal assembly that is configured to be securable to the distal end of the endoscope and that includes an endcap that is configured to engage the needle when the needle is advanced distally into the endcap and to release the needle when the needle is locked to the distal shuttle and the distal shuttle is withdrawn proximally and an elongate tool guide having a distal end disposed relative to the distal assembly, the elongate tool guide movable between a deployment configuration in which the elongate tool guide is substantially parallel with the distal assembly and a working configuration in which the elongate tool guide curves away from the distal assembly.

Alternatively or additionally, the elongate tool guide may include a guide structure that is fixedly secured to the distal assembly and a polymeric tubular member that is secured to the guide structure and extends proximally therefrom.

Alternatively or additionally, the elongate tool guide may move from its deployment configuration into its working configuration in response to a tool being extended distally through the elongate tool guide.

Alternatively or additionally, the elongate tool guide may include a guide structure that is pivotably secured to the distal assembly and a polymeric tubular member that is secured to the guide structure and extends proximally therefrom, the guide structure and the polymeric tubular member together defining a lumen. A pivot structure may protrude into the lumen such that a tool being extended distally through the elongate tool guide will contact the pivot structure, where further distal urging of the tool may cause the tool to interact with the pivot structure and cause the guide structure to pivot relative to the distal assembly, thereby moving the elongate tool guide from its deployment configuration into its working configuration.

Alternatively or additionally, the elongate tool guide may include an elongate structure defining at least a first lumen and a second lumen, the first lumen configured to accommodate a tool extending therethrough. A metallic ribbon may extend through the second lumen and may be movable between a linear configuration in which the metallic ribbon is straight and a remembered configuration in which the metallic ribbon is curved. The elongate structure may be straight when the metallic ribbon is straight and the elongate structure may be curved when the metallic ribbon is curved.

Alternatively or additionally, the elongate tool guide may include an elongate structure defining at least a first lumen and a second lumen, the first lumen configured to accommodate a tool extending therethrough. An elongate bi-stable member may extend through the second lumen and may be movable between a stable configuration in which the elongate bi-stable member is straight and an unstable configuration in which the metallic ribbon is curved. The elongate structure may be straight when the bi-stable metal element is straight and the elongate structure may be curved when the bi-stable metal element is curved.

Alternatively or additionally, the elongate tool guide may include a plurality of conduit segments that are joined together via living hinges formed between adjacent conduit segments of the plurality of conduit segments, each of the plurality of conduit segments including at least one control aperture extending through each conduit segment and at least one control cable extending through each of the at least one control aperture of each conduit segment. Applying an axial force to the at least one control cable may cause the elongate tool guide to move between its deployment configuration and its working configuration.

Another example is a suture device for use in combination with a delivery system including a lumen extending through the delivery system that includes a translation assembly that is configured to be axially translatable within the lumen of the delivery system, the delivery system including a distal end. The translation assembly includes a needle that is usable to carry a suture, a distal shuttle that is configured to releasably secure the needle and a user interface that extends proximally from the distal shuttle and is configured to enable a user to releasably secure the needle. A distal assembly is configured to be securable to the distal end of the delivery system and includes an endcap that is configured to releasably engage and disengage the needle, the endcap configured to engage the needle when the needle is advanced distally into the endcap, and to release the needle when the needle is locked to the distal shuttle and the distal shuttle is withdrawn proximally. The distal assembly includes a guide member that is configured to permit the suture translation assembly to extend through the guide member and to translate relative to the guide member and an elongate tool guide having a distal end disposed relative to the distal assembly, the elongate tool guide movable between a deployment configuration in which the elongate tool guide is substantially parallel with the distal assembly and a working configuration in which the elongate tool guide curves away from the distal assembly, the elongate tool guide including a guide structure fixedly secured to the distal assembly and a polymeric tubular member secured to the guide structure and extending proximally therefrom.

Another example is a medical device for use in combination with a delivery system including a lumen extending through the delivery system. The medical device includes an elongate tool guide adapted to be secured relative to a distal end of the delivery system in order to guide tools extended through the elongate tool guide, the elongate tool guide movable between a deployment configuration in which the elongate tool guide is substantially parallel with the delivery system when the elongate tool guide is secured relative to the distal end of the delivery system and a working configuration in which the elongate tool guide curves away from the distal assembly.

Alternatively or additionally, the elongate tool guide may include a guide structure that is adapted to be secured relative to the distal end of the delivery system and a polymeric tubular member that is secured to the guide structure and that extends proximally therefrom.

Alternatively or additionally, the guide structure may be adapted to be rigidly secured to an intervening structure between the guide structure and the distal end of the delivery system.

Alternatively or additionally, the elongate tool guide may be adapted to move from its deployment configuration into its working configuration in response to a tool being extended distally through the elongate tool guide.

Alternatively or additionally, the elongate tool guide may include a guide structure that is pivotably secured to an intervening structure between the guide structure and the distal end of the delivery system, a polymeric tubular member that is secured to the guide structure and extends proximally therefrom such that the guide structure and the polymeric tubular member together defining a lumen, and a pivot structure that protrudes into the lumen such that a tool being extended distally through the elongate tool guide will contact the pivot structure, where further distal urging of the tool will cause the tool to interact with the pivot structure and cause the guide structure to pivot relative to the distal assembly, thereby moving the elongate tool guide from its deployment configuration into its working configuration.

Alternatively or additionally, the elongate tool guide may include an elongate structure defining at least a first lumen and a second lumen, where the first lumen is configured to accommodate a tool extending therethrough and a metallic ribbon extends through the second lumen, the metallic ribbon movable between a linear configuration in which the metallic ribbon is straight and a remembered configuration in which the metallic ribbon is curved. The elongate structure is straight when the metallic ribbon is straight and the elongate structure is curved when the metallic ribbon is curved.

Alternatively or additionally, the elongate tool guide may include an elongate structure defining at least a first lumen and a second lumen, where the first lumen is configured to accommodate a tool extending therethrough and an elongate bi-stable member extends through the second lumen, the elongate bi-stable member movable between a stable configuration in which the elongate bi-stable member is straight and an unstable configuration in which the metallic ribbon is curved. The elongate structure is straight when the bi-stable metal element is straight and the elongate structure is curved when the bi-stable metal element is curved.

Alternatively or additionally, the elongate tool guide may include a plurality of conduit segments that are joined together via living hinges formed between adjacent conduit segments of the plurality of conduit segments, each of the plurality of conduit segments including at least one control aperture extending through each conduit segment and at least one control cable extending through each of the at least one control aperture of each conduit segment. Applying an axial force to the at least one control cable may cause the elongate tool guide to move between its deployment configuration and its working configuration.

Alternatively or additionally, the medical device may further include a distal assembly that is adapted to be secured relative to the distal end of the delivery system, with the elongate tool guide securable relative to the distal assembly, the distal assembly adapted to accommodate a suture device.

Alternatively or additionally, the suture device may include a suture translation assembly that is configured to be axially translatable within the lumen of the delivery system and a guide member that is configured to permit the suture translation assembly to extend through.

Alternatively or additionally, the suture translation assembly may include a needle usable to carry a suture, a distal shuttle configured to releasably secure the needle and a user interface extending proximally from the distal shuttle, the user interface configured to enable a user to releasably secure the needle. The suture device may further include an endcap configured to releasably engage and disengage the needle, the endcap configured to engage the needle when the needle is advanced distally into the endcap, and to release the needle when the needle is locked to the distal shuttle and the distal shuttle is withdrawn proximally.

Alternatively or additionally, the endcap may include a proximal needle opening configured to accommodate the needle when the needle is advanced distally into the endcap, the proximal needle opening aligned with a longitudinal axis of the needle, one or more securement openings arranged orthogonal to the proximal needle opening and one or more securements disposed within the securement openings, the one or more securements configured to releasably engage the distal detent of the needle.

Another example is a medical device for use in combination with an endoscope having a working channel and a distal end. The medical device includes a distal assembly that is adapted to be secured relative to the endoscope and an elongate tool guide having a distal end disposed relative to the distal assembly, the elongate tool guide movable between a deployment configuration in which the elongate tool guide is substantially parallel with the distal assembly and a working configuration in which the elongate tool guide curves away from the distal assembly.

Alternatively or additionally, the elongate tool guide may include a guide structure fixedly secured to the distal assembly and a polymeric tubular member secured to the guide structure and extending proximally therefrom.

Alternatively or additionally, the elongate tool guide may move from its deployment configuration into its working configuration in response to a tool being extended distally through the elongate tool guide.

Alternatively or additionally, the elongate tool guide may include a guide structure that is pivotably secured to the distal assembly, a polymeric tubular member that is secured to the guide structure and extends proximally therefrom, the guide structure and the polymeric tubular member together defining a lumen and a pivot structure that protrudes into the lumen such that a tool being extended distally through the elongate tool guide will contact the pivot structure, where further distal urging of the tool will cause the tool to interact with the pivot structure and cause the guide structure to pivot relative to the distal assembly, thereby moving the elongate tool guide from its deployment configuration into its working configuration.

Alternatively or additionally, the elongate tool guide may include an elongate structure defining at least a first lumen and a second lumen, where the first lumen is configured to accommodate a tool extending therethrough and a metallic ribbon extends through the second lumen, the metallic ribbon movable between a linear configuration in which the metallic ribbon is straight and a remembered configuration in which the metallic ribbon is curved. The elongate structure is straight when the metallic ribbon is straight and the elongate structure is curved when the metallic ribbon is curved.

Alternatively or additionally, the elongate tool guide may include an elongate structure defining at least a first lumen and a second lumen, where the first lumen is configured to accommodate a tool extending therethrough and an elongate bi-stable member extends through the second lumen, the elongate bi-stable member movable between a stable configuration in which the elongate bi-stable member is straight and an unstable configuration in which the metallic ribbon is curved. The elongate structure is straight when the bi-stable metal element is straight and the elongate structure is curved when the bi-stable metal element is curved.

Alternatively or additionally, the elongate tool guide may include a plurality of conduit segments joined together via living hinges formed between adjacent conduit segments of the plurality of conduit segments, each of the plurality of conduit segments including at least one control aperture extending through each conduit segment and at least one control cable extending through each of the at least one control aperture of each conduit segment. Applying an axial force to the at least one control cable causes the elongate tool guide to move between its deployment configuration and its working configuration.

Another example is a medical device for use in combination with a delivery system including a lumen extending through the delivery system. The medical device includes a distal assembly configured to be securable to the distal end of the delivery system and an elongate tool guide configured to be securable relative to the distal assembly, the elongate tool guide movable between a deployment configuration in which the elongate tool guide is substantially parallel with the distal assembly and a working configuration in which the elongate tool guide curves away from the distal assembly, the elongate tool guide including a guide structure fixedly secured to the distal assembly and a polymeric tubular member secured to the guide structure and extending proximally therefrom.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which.

Figure 1:
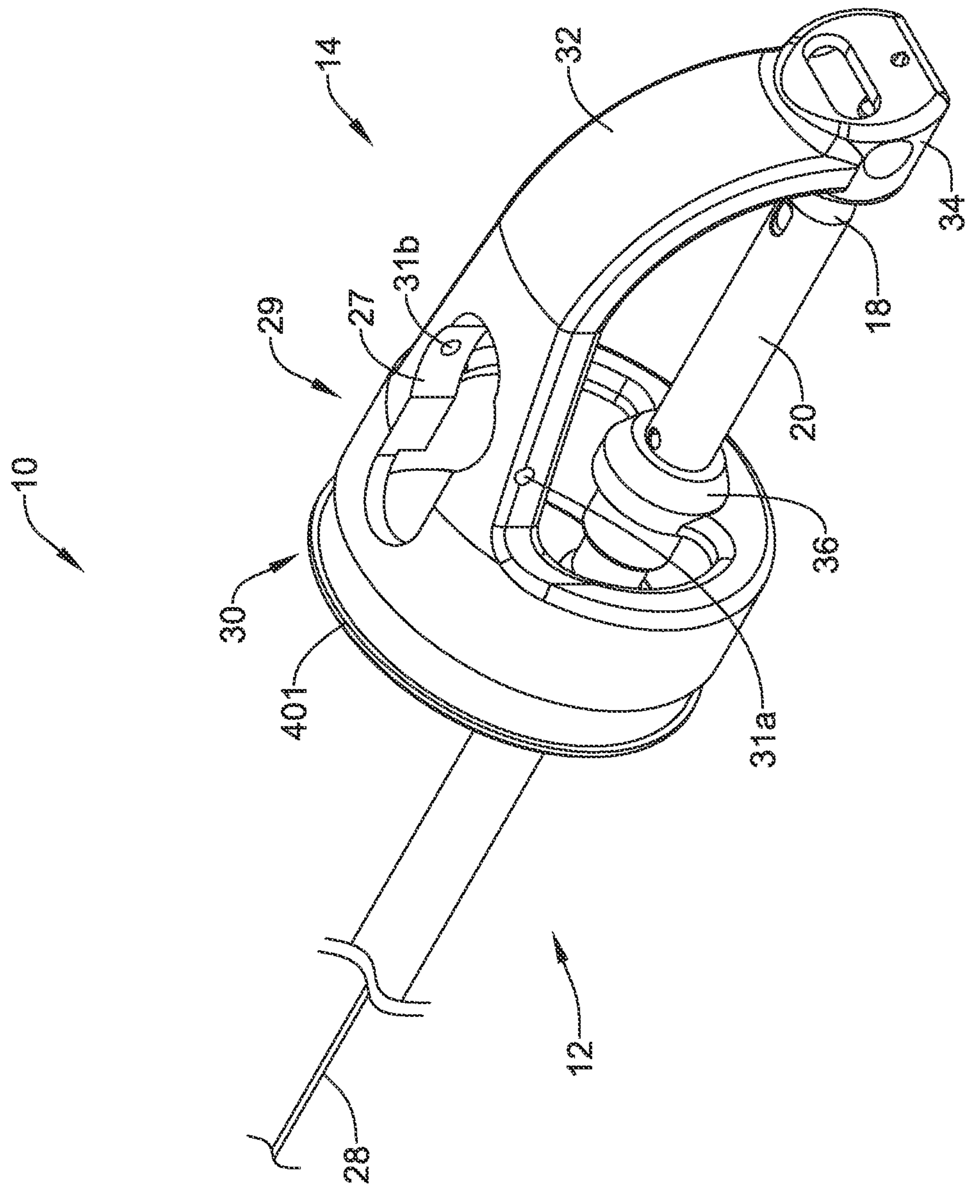
FIG. 1 is a perspective view of an illustrative suture device in accordance with an example of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

The disclosure pertains to devices that are configured to be used in combination with an endoscope or a similar delivery device for closing wounds within the body. In some instances, the suture devices described herein may be configured such that they may be used within a single working or available channel of an endoscope, and in some embodiments may be operated by a single individual, although in some embodiments a second individual may be involved. In some embodiments, the suture devices described herein may be considered as operating along a single line of operation. The device itself may be translatable distally and proximally within a working channel, and a handle portion may itself be translatable distally and proximally along the same line of operation in locking and unlocking a needle to be able to pass the needle back and forth between an active portion of the suture device and a passive portion of the suture device. The device may be configured to enable the needle to be selectively locked into either of a more distal position or a more proximal position, and the device may itself be translated distally or proximally with the needle locked in place in order to move the needle, and hence a suture, relative to the tissue being repaired.

FIG. 1 is a perspective view of a suture device 10 that may be considered as being configured for use in combination with a delivery system including a lumen that extends through the delivery system. For example, the delivery system may be an endoscope having a working channel. The delivery system may also be a catheter. It will be appreciated that there is a change in scale on either side of the break line shown. In some embodiments, the suture device 10 may be considered as including a suture translation assembly 12 that is configured to be axially translatable within the lumen of the delivery system and a distal assembly 14 that is configured to be secured to a distal end of the delivery system. The suture translation assembly 12 extends into the distal assembly 14 and includes a needle 16 that may be used to carry a suture as well as a distal shuttle 18 that is configured to releasably secure the needle 16.

A member 20 may be disposed over the distal shuttle 18 and, as will be shown in subsequent Figures, is movable between a locked position in which the needle 16 is secured to the distal shuttle 18 and an unlocked position in which the needle 16 is releasable from the distal shuttle 18. In some embodiments, for example, the member 20 may be a sleeve 20. A user interface may extend proximally from the distal shuttle 18 and the sleeve 20, and may be configured to move the sleeve 20 between the locked position and the unlocked position. A shaft 28 may extend distally to the suture translation assembly 12, and may in particular be coupled to the sleeve 20. The user interface may take a number of different forms. For examples, the user interface may be the user interface 22 as described and illustrated in U.S. Patent Application Publication No. 2018/0235604, which publication is incorporated by reference herein in its entirety. In some embodiments, the user interface may be as described in a provisional application Ser. No. 62/794,075 filed Jan. 18, 2019 and entitled ENDOSCOPIC SUTURING CONTROL HANDLE, which application is incorporated by reference herein in its entirety. In some embodiments, the user interface may be as described in a provisional application Ser. No. 62/848,853 filed May 16, 2019 and entitled CONTROL HANDLE FOR ENDOSCOPIC SUTURING, which application is incorporated by reference herein in its entirety. These are just examples.

In some embodiments, the distal assembly 14 includes a body 29 having a proximal connector 30 that may be configured to be coupled to the distal end of an endoscope or other delivery system. In some embodiments, as illustrated, the proximal connector 30 may include a fixation feature 401. As will be discussed with respect to subsequent Figures, the fixation feature 401, which may in some embodiments be considered as being a fixation flange 401, helps to secure the distal assembly 14 to the distal end of an endoscope or other delivery system using a split ring attachment mechanism.

The body 29 includes an arm 32 that extends to an endcap 34. As will be discussed, the endcap 34 may be configured to releasably engage and disengage the needle 16. In some embodiments, for example, the endcap 34 may be configured to engage the needle 16 when the needle 16 is advanced distally into the endcap 34, and to release the needle 16 when the needle 16 is locked into the distal shuttle 18 (as will be discussed) and the distal shuttle 18 is withdrawn proximally. The distal assembly 14 may be considered as including a guide member 36 that may be secured to or integrally formed with the body 29, and may permit the suture translation assembly 12 to extend through the guide member 36 and to translate relative to the guide member 36. In some embodiments, the body 29 may include an aperture 27 that may enable other devices to be inserted through the aperture 27. In some instances, as will be discussed with respect to subsequent Figures, the aperture 27 may be configured to accommodate a side-saddled lumen attachment element. In some embodiments, the aperture 27 may include one or more of a pin aperture 31*a* and a pin aperture 31*b* that may, for example, be used to mount the aforementioned side-saddled lumen attachment element, or possibly other features as well.

Figure 2:
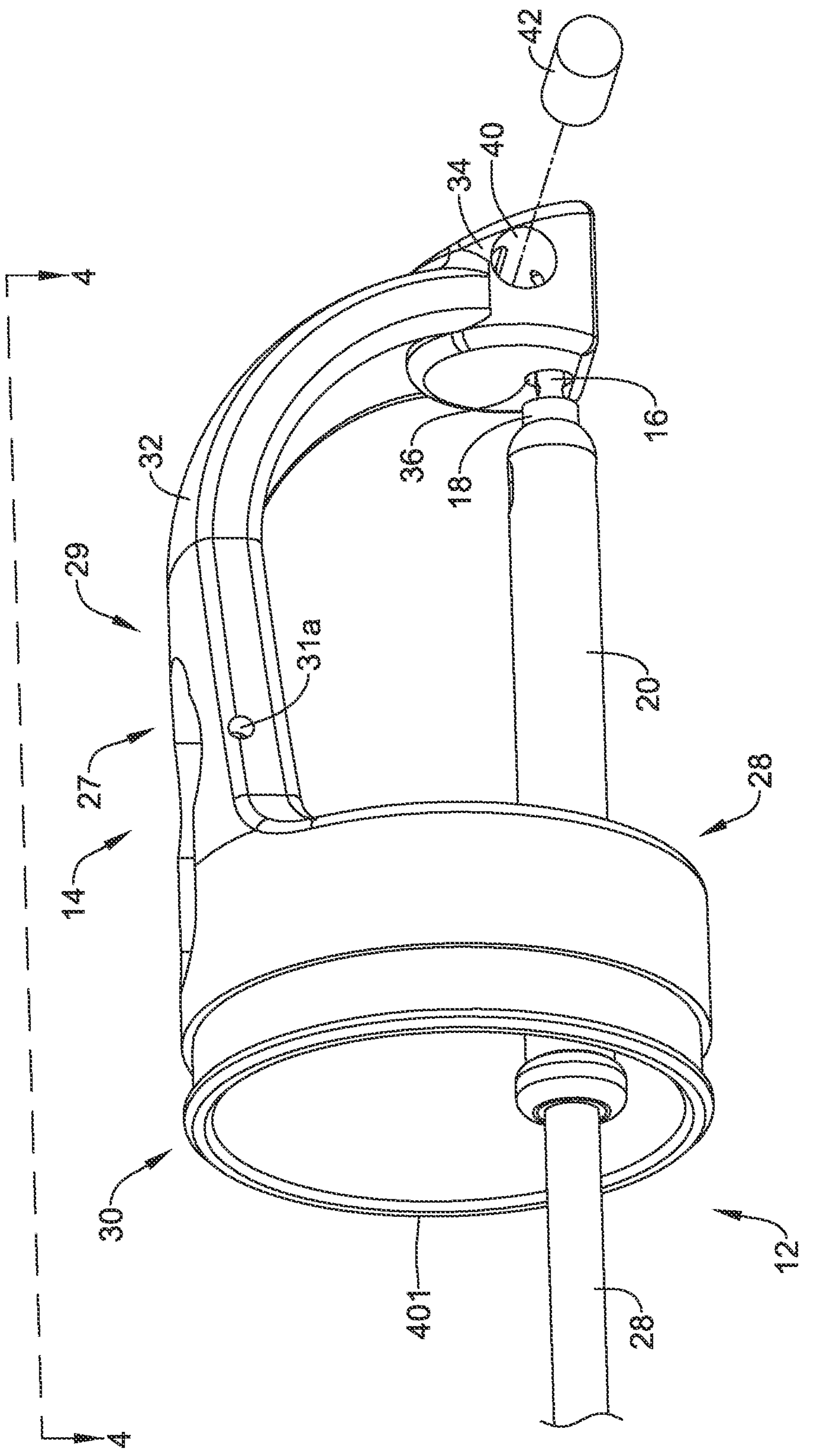
FIG. 2 is a perspective view of a distal assembly forming part of the illustrative suture device of FIG. 1, shown in an extended position.
Figure 3:
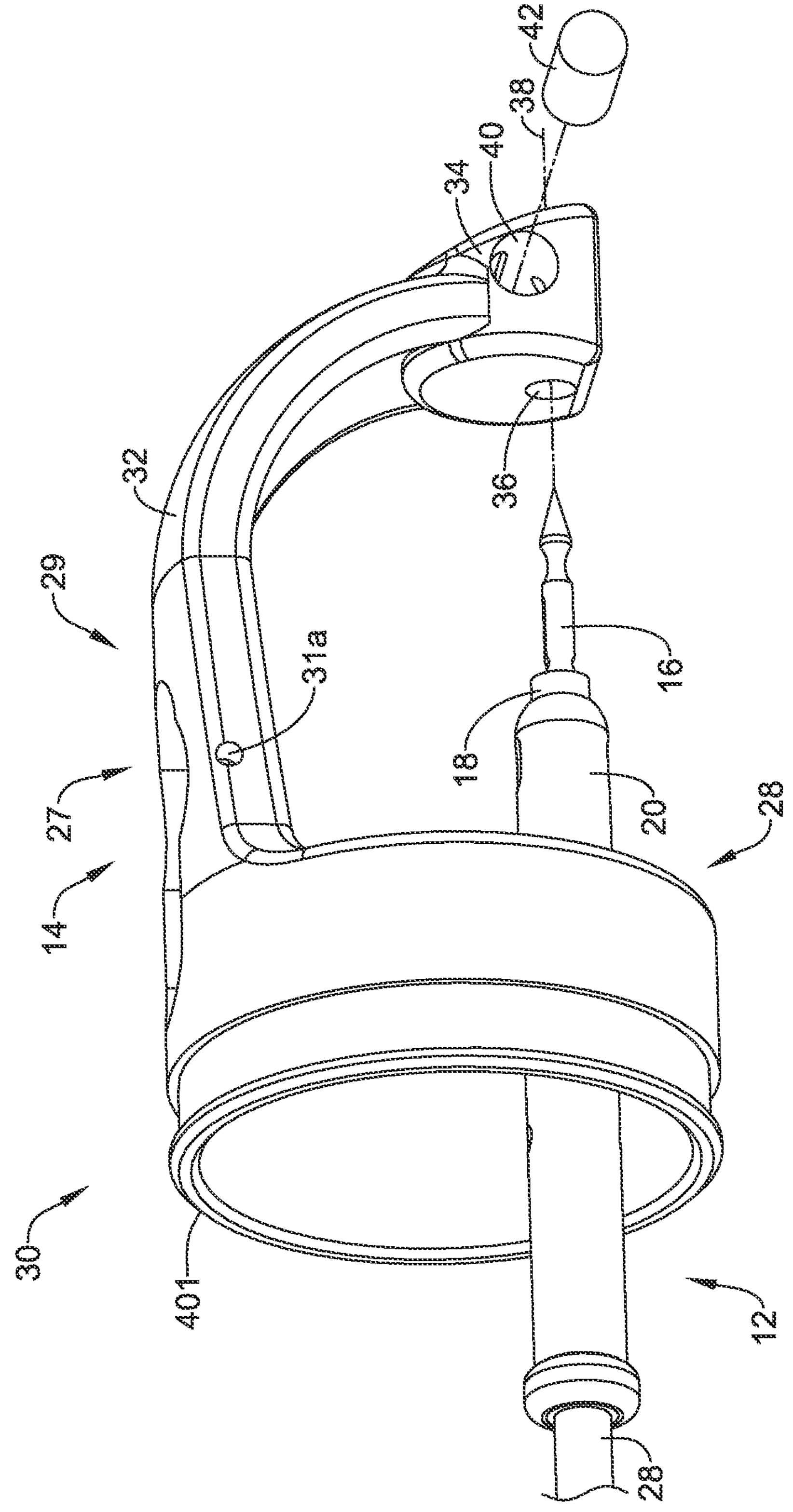
FIG. 3 is a perspective view of the distal assembly of FIG. 2, shown in a retracted position.

FIG. 2 and FIG. 3 show the suture translation assembly 12 extended through the guide member 36 and into the distal assembly 14. In FIG. 2, the suture translation assembly 12 is shown in an extended position in which the needle 16 extends into the endcap 34 while in FIG. 3, the suture translation assembly 12 is shown in a retracted position in which the needle 16 has been withdrawn proximally from the endcap 34. In some embodiments, as can be seen, the endcap 34 includes a proximal needle opening 37 that is configured to help guide the needle 16 into the proximal needle opening 37 as well as to accommodate the needle 16 when the needle 16 is advanced distally into the endcap 34. In some embodiments, the proximal needle opening 37 may extend all the way through the endcap 34 while in other cases the proximal needle opening 37 may not pass all the way through the endcap 34. In some instances, as shown, the proximal needle opening 37 may be considered as being aligned with a longitudinal axis 38 of the needle 16 (as shown in FIG. 3).

One or more securement openings 40 may be arranged orthogonal to the proximal needle opening 37 and one or more securements 42 that are configured to be disposed within the one or more securement openings 40, and which are configured to releasably engage the distal detent (as will be discussed) of the needle 16. In some embodiments, there may be a pair of securement openings 40, one on either side of the endcap 34. In some embodiments, there may be a pair of securements 42, with one disposed within each of the pair of securement openings 40. In some embodiments, while shown schematically, the one or more securements 42 may be springs or coils, for example.

Figure 4:
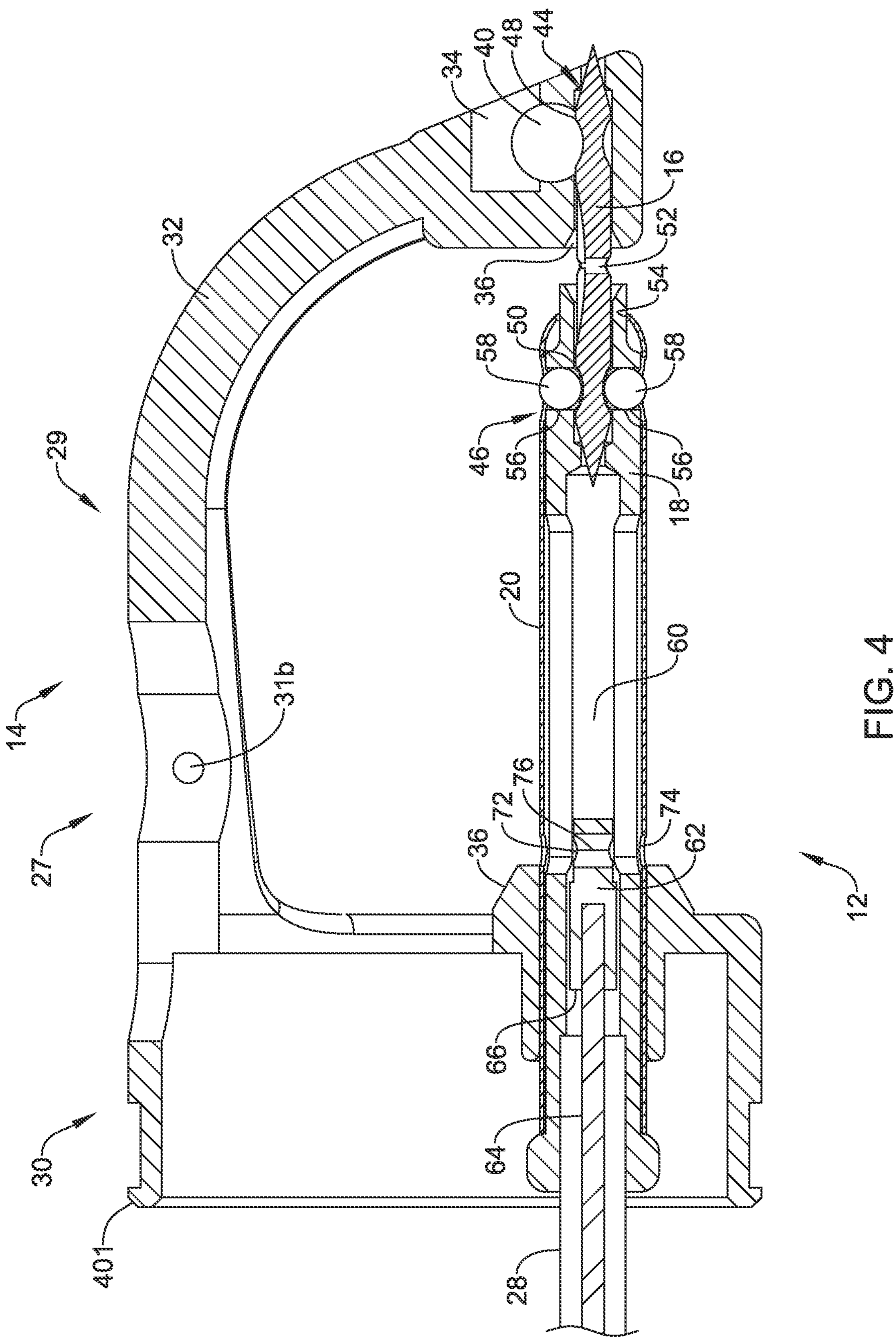
FIG. 4 is a cross-sectional view of the distal assembly of FIG. 2, taken along the line 4-4.
Figure 5:
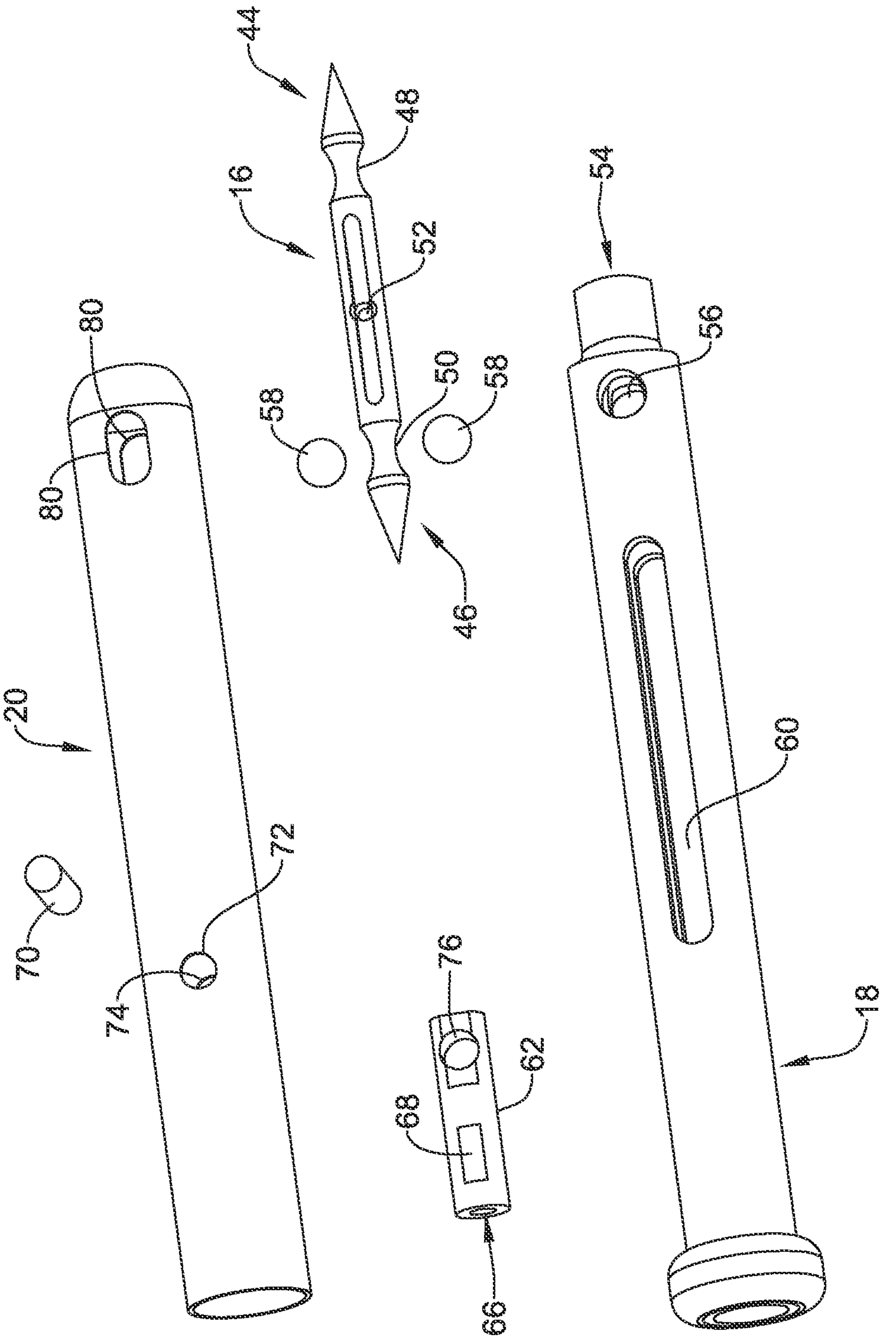
FIG. 5 is an exploded view of a portion of a suture translation assembly forming part of the illustrative suture device of FIG. 1.

FIG. 4 is a cross-sectional view of the distal assembly 14, with the suture translation assembly 12 disposed within the distal assembly 14. FIG. 5 is an exploded view of the suture translation assembly 12. The needle 16 may be considered as including a distal region 44 and a proximal region 46. In some embodiments, the distal region 44 may include a distal detent 48 for releasably engaging the endcap 34 and the proximal region 46 may include a proximal detent 50 for releasably engaging the distal shuttle 18. The needle 16 may, as shown, include an aperture 52 for accommodating a suture line passing therethrough.

In some embodiments, the distal shuttle 18 may be considered as including a distal needle opening 54 that is configured to accommodate the needle 16 when the distal shuttle 18 is advanced distally over the needle 16 and that is aligned with the longitudinal axis 38 of the needle 16. One or more bearing ball openings 56 may be arranged orthogonal to the distal needle opening 54 such that the one or more bearing ball openings 56 align with the proximal detent 50 when the needle 16 is secured to the distal shuttle 18. In some embodiments, one or more bearing balls 58 may be disposed within the one or more bearing ball openings 56 and may be configured to be disposed within the proximal detent 50 when the needle is secured to the distal shuttle 18.

In some embodiments, the distal shuttle 18 includes an internal void 60 and a sleeve capture member 62 that is slidingly disposed within the internal void 60. In some embodiments, the sleeve capture member 62 may be coupled to a cable 64 extending distally within the shaft 28 and into a cable aperture 66 and secured via a crimp or other mechanical connection 68. In some embodiments, the sleeve capture member 62 may be coupled to the sleeve 20 via a pin 70 that extends through first and second sleeve connection apertures 72, 74 and a corresponding aperture 76 extending through the sleeve capture member 62 as well as extending through the internal void 60.

Figure 6:
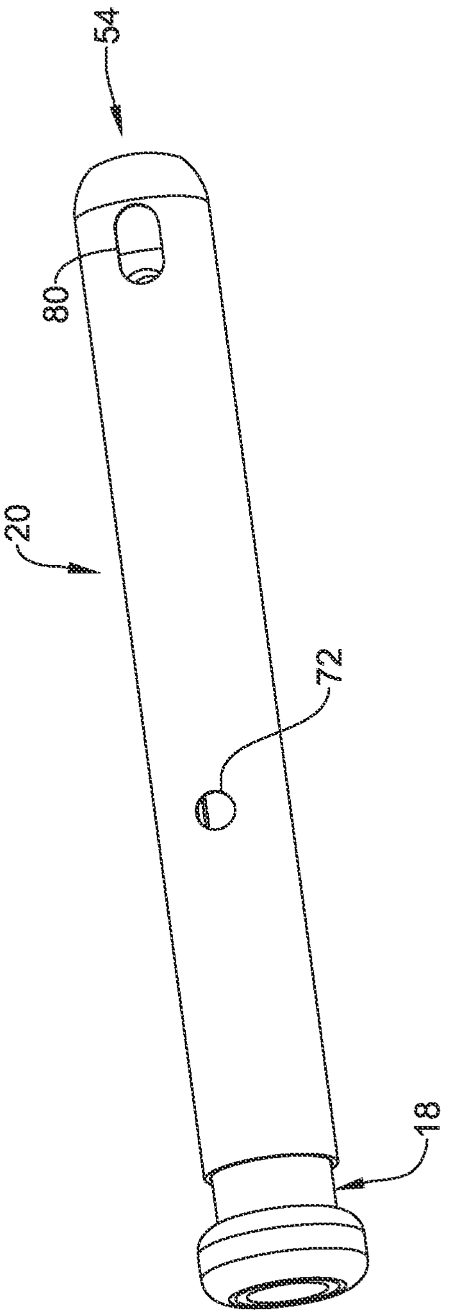
FIG. 6 is a side view of a distal shuttle and a member forming part of the suture translation assembly, with the member shown extended in a locked position.

In some embodiments, the sleeve 20 includes one or more sleeve openings 80 that may be smaller in diameter, or smaller in width, than the diameter of the one or more bearing balls 58. In some embodiments, the sleeve 20 may include a pair of sleeve openings 80, corresponding to a pair of bearing ball openings 56 and a pair of bearing balls 58. When the sleeve 20 is in the locked position, as shown for example in FIG. 6, the one or more sleeve openings 80 are misaligned with, or do not align with, the one or more bearing ball openings 56, and so the one or more bearing balls 58 engage the proximal detent 50 of the needle 16. The sleeve 20 prevents the one or more bearing balls 58 from being pushed out of the proximal detent 50.

Figure 7:
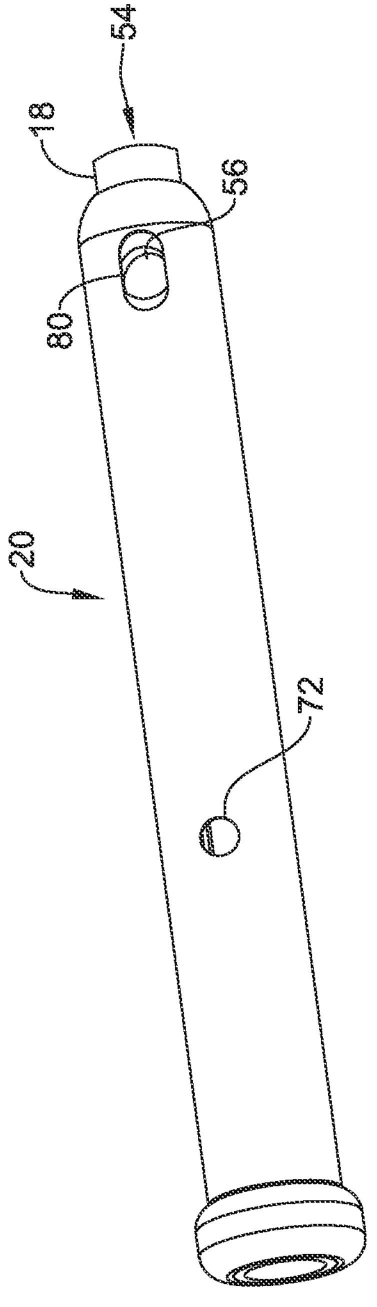
FIG. 7 is a side view of the distal shuttle and the member of FIG. 6, with the member shown retracted in an unlocked position.

Conversely, when the sleeve 20 is in the unlocked position, as shown for example in FIG. 7, the one or more sleeve openings 80 are aligned with the one or more bearing ball openings 56. This permits the one or more bearing balls 58 to move radially out, into the one or more sleeve openings 80, a distance sufficient to permit the one or more bearing balls 58 to clear the proximal detent 50 of the needle 16 in response to a force applied to the one or more bearing balls 58 by the needle 16. With reference to FIG. 4, while the suture translation assembly 12 is shown advanced into the distal assembly 14, the sleeve 20 is in the unlocked position relative to the distal shuttle 18, and thus the one or more bearing balls 58 may be seen as extending partially into the one or more sleeve openings 80.

In some embodiments, it will be appreciated that the distal shuttle 18, and the sleeve 20, in combination, provide an active connection to the needle 16 while the distal endcap 34 provides a passive connection to the needle 16. If the needle 16 is moved distally into the distal endcap 34, the distal endcap 34 will grab onto the needle 16, with the one or more securements 42 engaging the distal detent 48. If the needle 16 is subsequently moved proximally, the axial force applied overcomes any resistance provided by the one or more securements 42, and the needle 16 is able to move proximally. In contrast, the active connection to the needle 16 provided by the distal shuttle 18 and the sleeve 20, however, requires action to move the sleeve 20, relative to the distal shuttle 18, between the locked position and the unlocked position. The user interface provides a mechanism for positively moving the sleeve 20 between the locked and unlocked positions.

Figure 8:
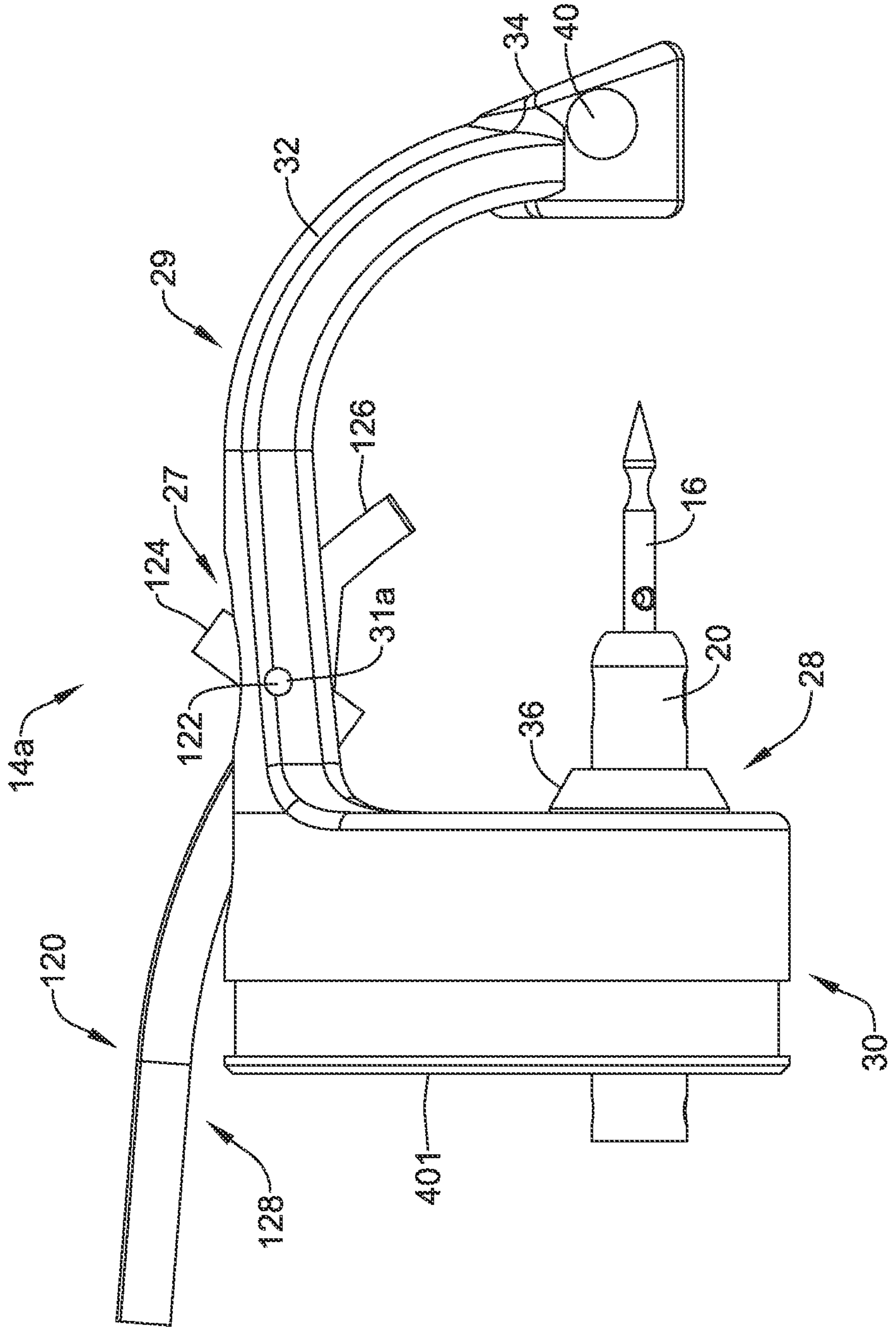
FIG. 8 is a side view of a distal assembly usable in the suture device of FIG. 1 in accordance with an example of the disclosure.

FIG. 8 is a side view of a distal assembly 14*a* that may, for example, be usable in the suture device 10 shown in FIG. 1. The distal assembly 14*a* is similar to the distal assembly 14 shown in previous Figures, but includes a side-saddled lumen attachment element 120 that is coupled to the body 29 of the distal assembly 14*a*. In some embodiments, the side-saddled lumen attachment element 120 may include one or two pegs 122 that fit into the pin apertures 31*a* and 31*b* (pin aperture 31*a* is visible in this view) and thus enable the side-saddled lumen attachment element 120 to pivot relative to the body 29 of the distal assembly 14*a*. In some embodiments, the side-saddled lumen attachment element 120 includes a ring 124, from which the pegs 122 extend, a distal region 126 and a body 128 that in some instances has a curvature to it.

Figure 9:
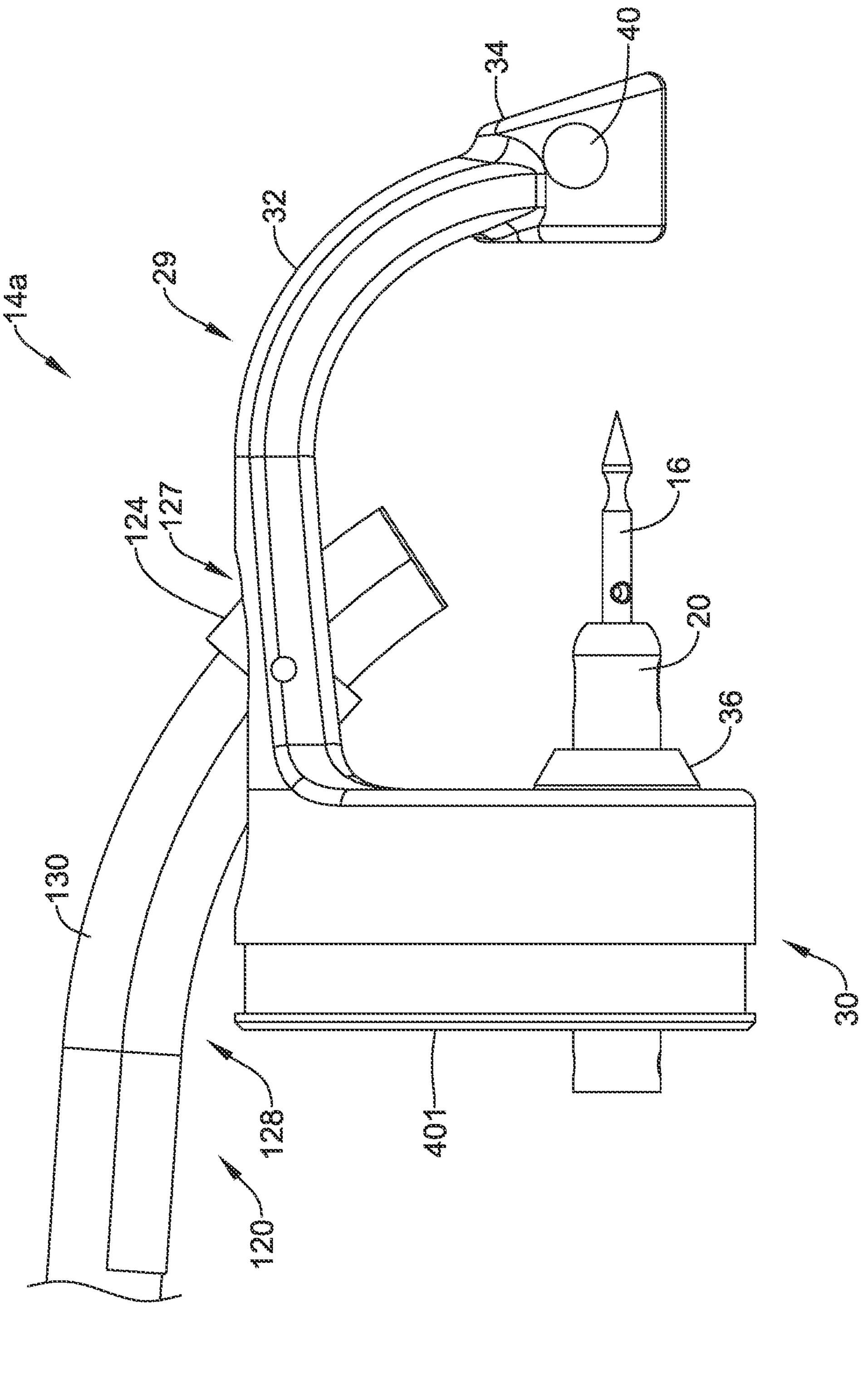
FIG. 9 is a side view of the distal assembly of FIG. 8 in combination with an attached flexible lumen.

In some embodiments, the distal region 126 and the body 128 have a semi-circular profile in order to accommodate a lumen such as a flexible lumen 130 that may engage within the side-saddled lumen attachment element 120 via a frictional or compressive fit as shown in FIG. 9. The flexible lumen 130 may be polymeric or metallic. A polymeric lumen may, for example, be expanded to a full working dimension by extending a mandrel through the flexible lumen 130 after the flexible lumen 130 has been placed relative to the side-saddled lumen attachment element 120.

In some embodiments, the side-saddled attachment element 120 (and accompanying flexible lumen 130) may be used as a secondary working channel and may contain the suture used in the procedure. In some embodiments, it may be large enough to accommodate secondary tools for use during the procedure for tissue acquisition or manipulation allowing secondary tool use without requiring a dedicated dual-channel delivery system such as a dual channel endoscope. If desired, a dual-channel delivery system could be used to provide even more options in a procedure. The side-saddled attachment element 120 may have an exit port in the distal assembly 14*a* such that secondary tools extend along an axis suitable for tissue manipulation. This axis may cross the axis of the suture carrying element, allowing a secondary tool to pull tissue into the suture carrying element's projected path. For example, this could be used to pull tissue in line with a needle to assist in driving the needle 16 through the tissue. Maintaining tension on the suture through the side-saddled attachment element 120 may keep the suture from interfering with the procedure.

Figure 10:
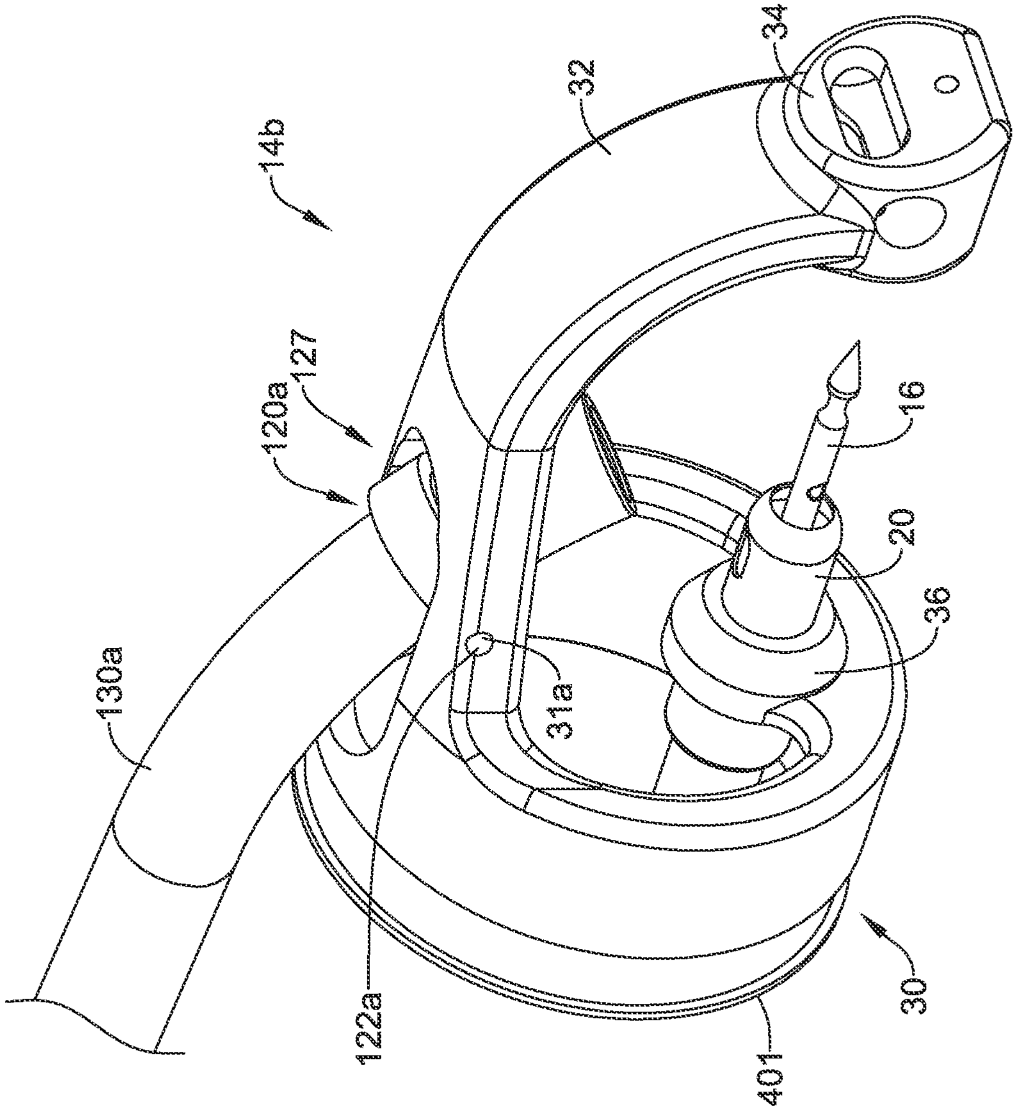
FIG. 10 is a side view of a distal assembly usable in the suture device of FIG. 1, shown with an attached lumen, in accordance with an example of the disclosure.

FIG. 10 is a perspective view of a distal assembly 14*b* that includes a shorter side-saddled lumen attachment element 120*a* that may be pivotally secured to the body 29 via one or more pegs 122*a* that extend into the pin apertures 31*a*, 31*b*. A lumen 130*a* coupled with the side-saddled lumen attachment element 120*a* to provide a working channel through which the suture or other tools may be extended.

Figure 11:
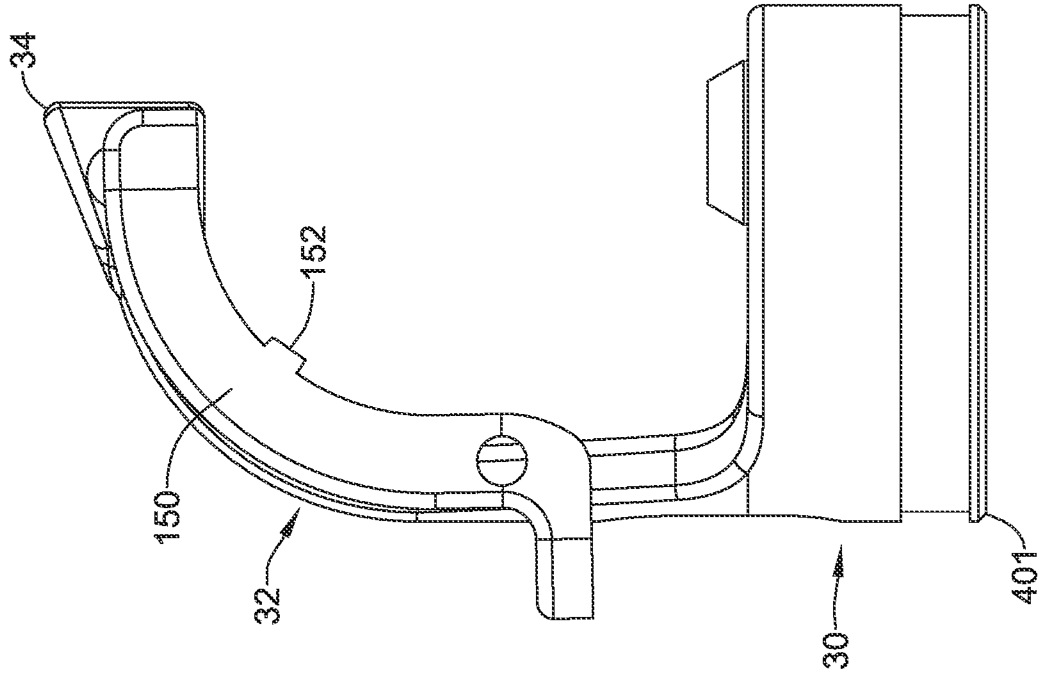
FIGS. 11 and 12 are views of a tissue release mechanism that may be used in combination with the distal assemblies of FIGS. 1 and 8 in accordance with an example of the disclosure.
Figure 12:
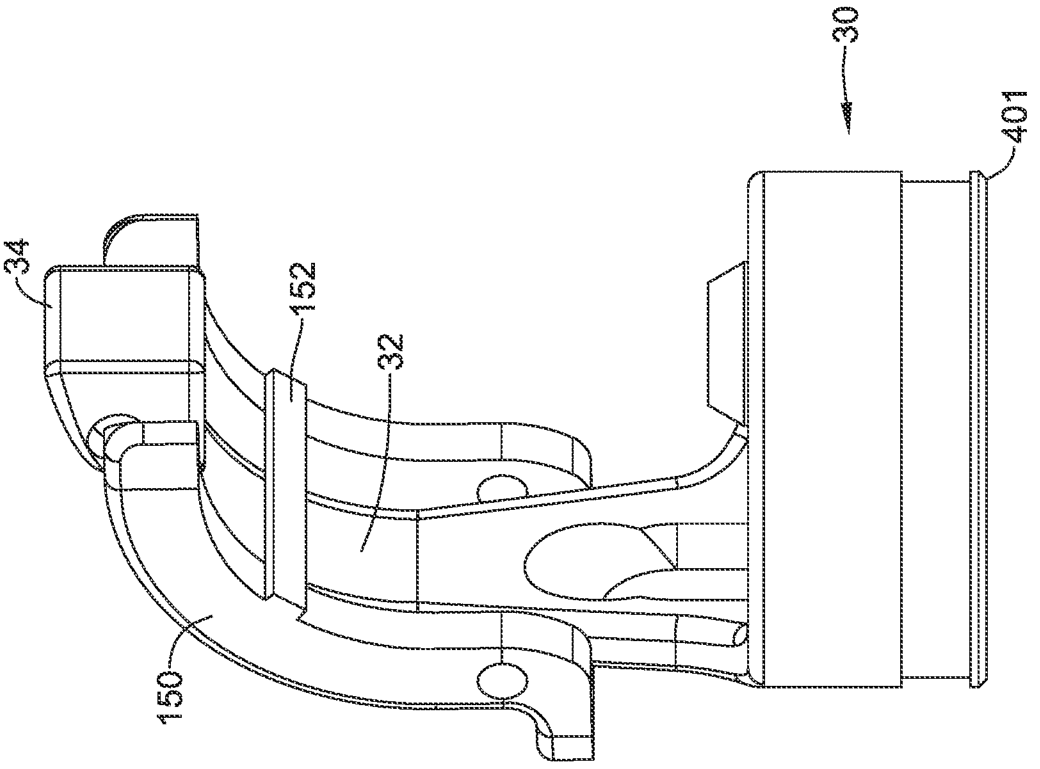

FIG. 11 and FIG. 12 are views of a tissue release mechanism 150 that may fit over the arm 32. In some embodiments, the tissue release mechanism 150 may assist in a procedure by helping to remove tissue that may otherwise become stuck on the needle 16. In some instances, the tissue release mechanism 150 may be spring-loaded to engage the needle 16, or may be separately and independently actuated. In some instances, the tissue release mechanism 150 includes a cross-bar 152 that provides an additional surface that can push tissue off of the needle 16.

In preparing the suture device 10 for use, the distal assembly 14 may be secured to a delivery device such as an endoscope. In some embodiments, an attachment enabler, such as a flexible silicone tube, may be unrolled along the delivery device in order to hold the distal assembly 14 in place and to prevent rotation of the distal assembly 14 relative to the delivery device. In some embodiments, if desired, the side-saddled lumen attachment element 120 (or 120*a*) may be secured to the distal assembly 14. The suture may be passed through the needle 16, and fed back towards the user interface. The device 10 may be extended through the body to the defect site.

Figure 13:
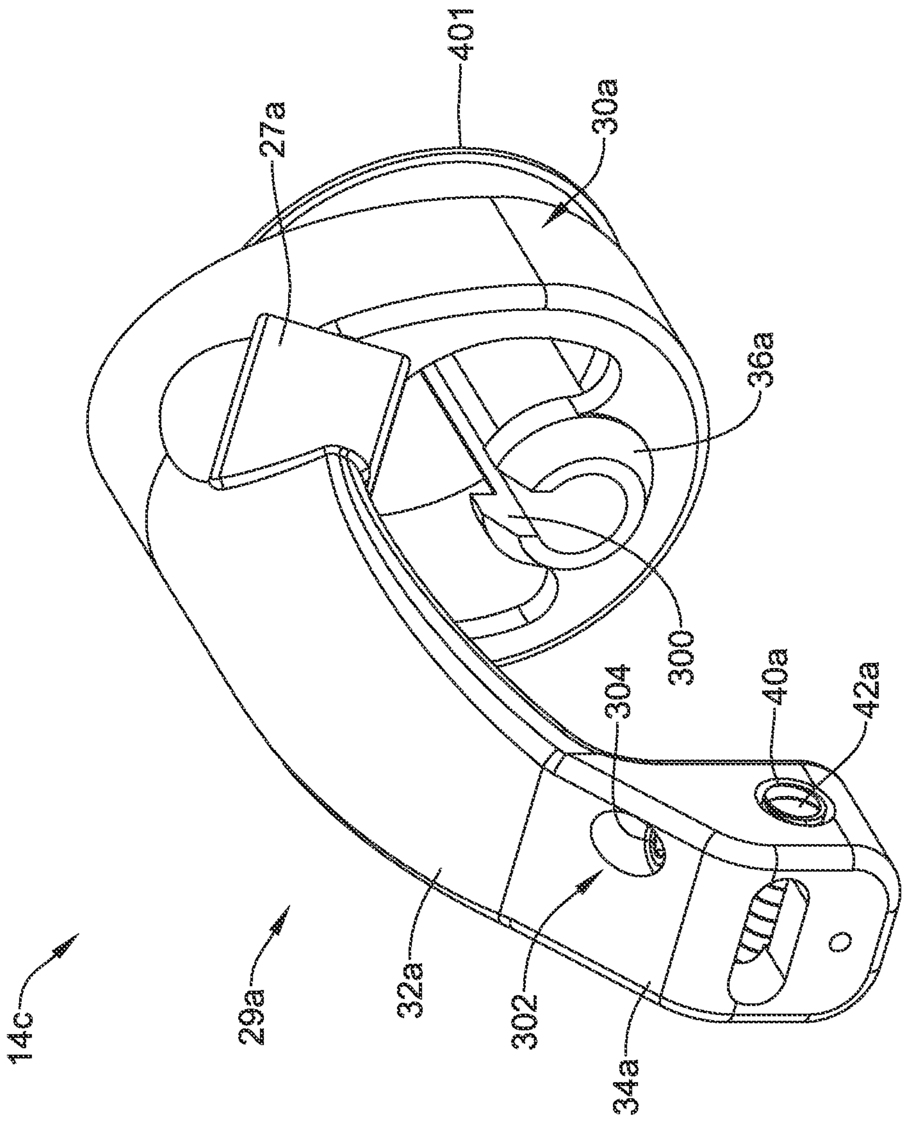
FIG. 13 is a perspective view of a distal assembly usable in the suture device of FIG. 1 in accordance with an example of the disclosure.

FIG. 13 is a perspective view of a distal assembly 14*c* that may, for example, be usable in the suture device 10 shown in FIG. 1. The distal assembly 14*c* is similar to the distal assembly 14 shown in previous Figures, but includes several modifications that may be useful, particularly in bariatric revision procedures. A bariatric procedure commonly refers to a procedure in which the effective useful volume of a patient's stomach may be surgically reduced in order to effect long-term weight loss for the patient and may be performed laparoscopically. A bariatric revision procedure is a procedure, performed endoscopically, in which changes may be made to what was originally done to the patient's stomach. In some embodiments, the distal assembly 14*c* may also be used in other suturing procedures, such as but not limited to full tissue thickness repairs and/or partial tissue thickness repairs.

The distal assembly 14*c* may include a body 29*a* having a proximal connector 30*a* that may be configured to be coupled to the distal end of an endoscope or other delivery system, for example. In some embodiments, as illustrated, the proximal connector 30*a* may include a fixation feature such as a fixation flange 401. The body 29*a* includes an arm 32*a* that extends to an endcap 34*a*. In some embodiments, the body 29*a*, including the arm 32*a*, may be similar to the body 29 and arm 32 referenced previously with respect to the distal assembly 14, the distal assembly 14*a* and the distal assembly 14*b*. In some instances, however, the body 29*a* and the arm 32*a* may be adapted to accommodate thicker tissue, which may for example mean a change in the overall shape of the body 29*a* and/or the arm 32*a* relative to the body 29 and/or the arm 32. In some embodiments, the body 29*a* and/or the arm 32*a* may simply be larger in order to accommodate thicker tissue. The distal assembly 14*c* may be considered as including a guide member 36*a* that may be secured to or integrally formed with the body 29*a*, and may be configured to permit a suture translation assembly (such as the suture translation assembly 12, a suture translation assembly 12*a*, shown in FIG. 14 through FIG. 18, or a suture translation assembly 12*b*, shown in FIG. 19 through FIG. 22) to extend through the guide member 36*a* and to translate relative to the guide member 36*a*.

In some embodiments, as illustrated, the guide member 36*a* includes a channel 300. In some embodiments, the channel 300 permits a suture to pass between the suture translation assembly 12, 12*a*, 12*b* and a working channel of the endoscope or other delivery device to which the distal assembly 14*c* is attached. The channel 300 may, for example, be designed to include a lead in that would help to align the suture with the channel 300 when passing the suture translation assembly 12, 12*a*, 12*b* through the working channel of the endoscope or other delivery device. In some embodiments, there may be a desire to load the suture before passing the suture translation assembly 12, 12*a*, 12*b* through the working channel of the endoscope or other delivery device.

In some instances, the distal assembly 14*c* includes a guide structure 27*a* that is attached to or integrally formed with the body 29*a*. In some embodiments, the guide structure 27*a* may instead be pivotably attached to the body 29*a*. The guide structure 27*a* may be configured to accommodate a polymeric tubular member attached thereof, in order to guide tools through the endoscope and into position relative to the working site. In some instances, the guide structure 27*a* may be configured to accommodate a metallic tubular member attached thereto. In some embodiments, for example, the guide structure 27*a* and accompanying tubular member (not illustrated) may accommodate a graspers or similar tool that allows a user to grasp tissue and pull it into position so that the needle 16 may be passed through the tissue. In some embodiments, the relative position, or offset of the guide structure 27*a*, relative to the relative position or offset illustrated with respect to the distal assembly 14, the distal assembly 14*a* or the distal assembly 14*b*, may be greater in order to provide more room for tools and/or to accommodate larger and/or thicker portions of tissue.

The end cap 34*a* includes one or more securement openings 40*a* that may be, as can be seen, be arranged orthogonally to a proximal needle opening (not illustrated), such as the proximal needle opening 37 illustrated for example in FIG. 3. One or more securements 42*a* may correspondingly be disposed within the one or more securement openings 40*a*. In some embodiments, the one or more securements 42*a* may be a coil spring that is disposed within the one or more securement openings 40*a*. The securement 42*a* may releasably engage a detent on the needle 16, as discussed with respect to the distal assembly 14.

In some embodiments, the securement opening 40*a* may have a diameter that is greater than an overall diameter of the securement 42*a* and the securement opening 40*a* may taper to a diameter on an opposing side (not seen) that is about the same as the diameter of the securement 42*a*. In some embodiments, the securement 42*a* may be welded, soldered, adhesively secured or otherwise attached at the left side of the securement opening 40*a*, and may be free to move somewhat at the right side of the securement opening 40*a*. In some instances, the distal assembly 14*c* may include an opening 302 that is orthogonal to the securement opening 40*a*. The opening 302 may be threaded in order to threadedly engage a set screw 304. In some embodiments, as illustrated, the opening 302 may be offset closer to the right side of the securement opening 40*a*, away from the secured end of the securement 42*a*, such that the set screw 304 may be considered as supporting the free end of the securement 42*a*. Rotating the set screw 304 in a first direction, such as clockwise, may cause the set screw 304 to translate towards the securement 42*a*, thereby increasing an interference between the securement 42*a* and the needle 16 and increasing a retentive force that can be applied to the needle 16. Conversely, rotating the set screw in a second direction, such as counter-clockwise, may cause the set screw 304 to translate away from the securement 42*a*, thereby decreasing the retentive force that can be applied to the needle 16. This may help to adjust for manufacturing tolerances, for example.

Figure 14:
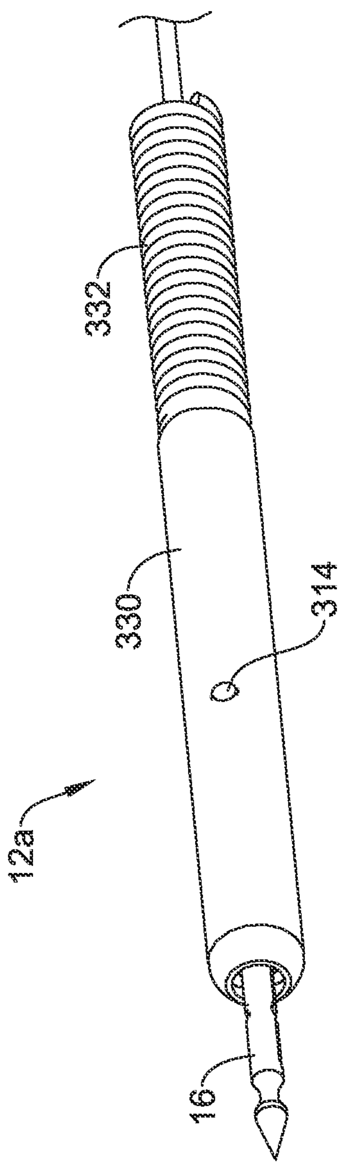
FIG. 14 is a perspective view of a suture translation assembly usable in the suture device of FIG. 1 in accordance with an example of the disclosure.
Figure 15:
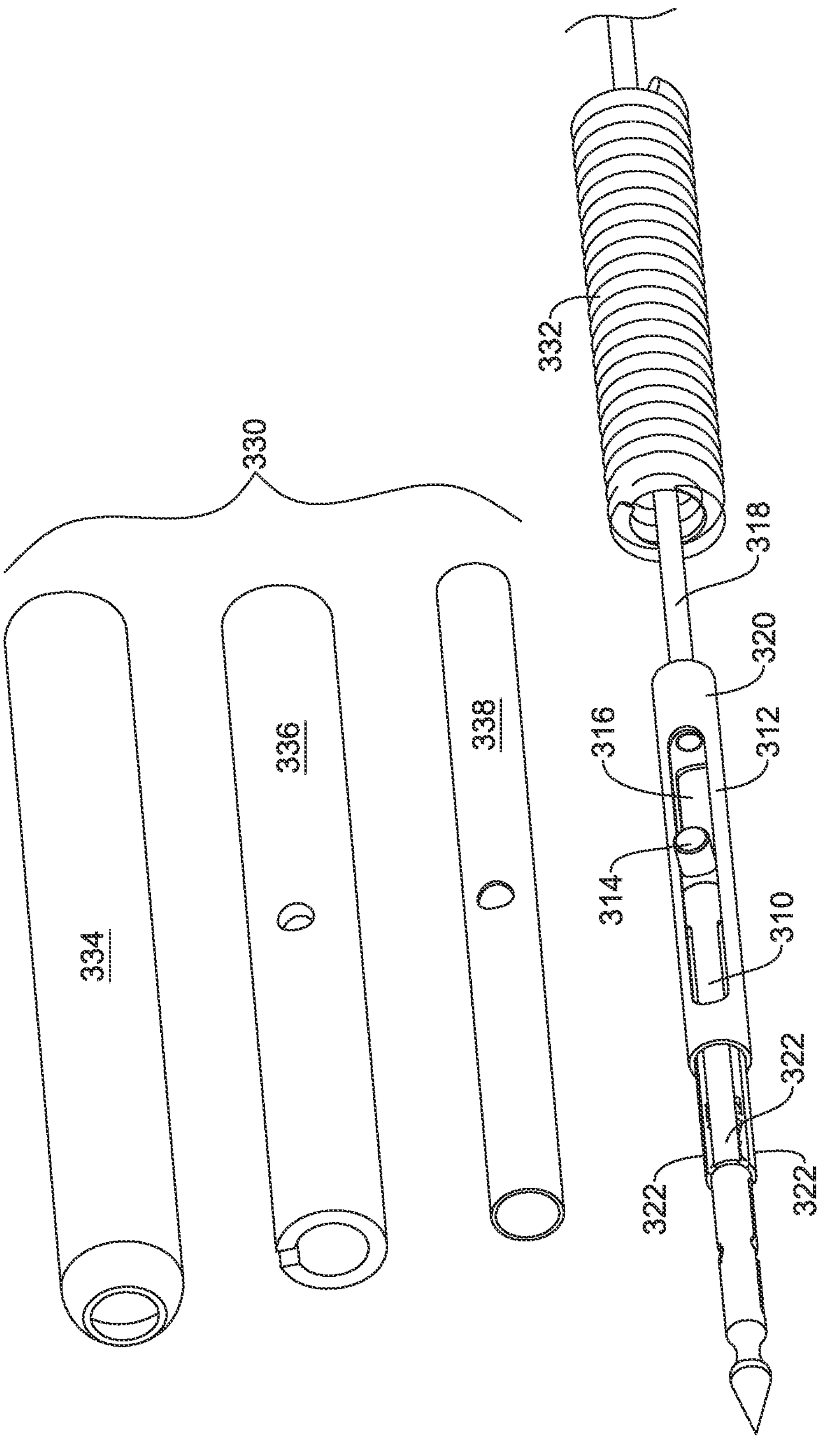
FIG. 15 is a partially exploded perspective view of the suture translation assembly of FIG. 14 in accordance with an example of the disclosure.

As noted, the distal assembly 14*c* may be used in combination with the suture translation assembly 12 discussed previously with respect to FIG. 5, for example. The distal assembly 14*c* may also be used with a suture translation assembly 12*a*, shown in FIG. 14 through FIG. 18, as well as with a suture translation assembly 12*b*, shown in FIG. 19 through FIG. 22. FIG. 14 is a perspective view of the suture translation assembly 12*a*, shown holding the needle 16, while FIG. 15 is a partially exploded view of the suture translation assembly 12*a*. As better seen in FIG. 15, the suture translation assembly 12*a* includes an inner member 310 that hold the needle 16. A locking member 312 is slidingly disposed over the inner member 310. As can be seen, the inner member 310 includes a pin 314 that extends radially outwardly from the inner member 310 and extends through a corresponding slot 316 that is formed in the locking member 312. The pin 314 serves to prevent relative rotation between the inner member 310 and the locking member 312. The pin 314 also serves to limit translation of the locking member 312 relative to the inner member 310.

A control member 318 is secured relative to a proximal end 320 of the locking member 312, and extends distally to a handle such as the translating handle 26 (FIG. 1). As a result, the locking member 312 may be translated distally and/or proximally relative to the inner member 310. As seen in FIG. 14, the suture translation assembly 12*a* includes an outer sleeve 330 that may be pinned via the pin 314 to the inner member 310. The outer sleeve 330 may be coupled with a coil 332, for example. In some embodiments, the outer sleeve 330 may be a single tubular member. In some embodiments, as shown for example in FIG. 15, the outer sleeve 330 may actually include one or more of an outer sleeve 334, a slotted sleeve 336, and an inner outer sleeve 338. The slotted sleeve 336 may be configured to permit a suture to pass therethrough. This is merely illustrative, and is not intended to be limiting in any fashion.

Figure 16:
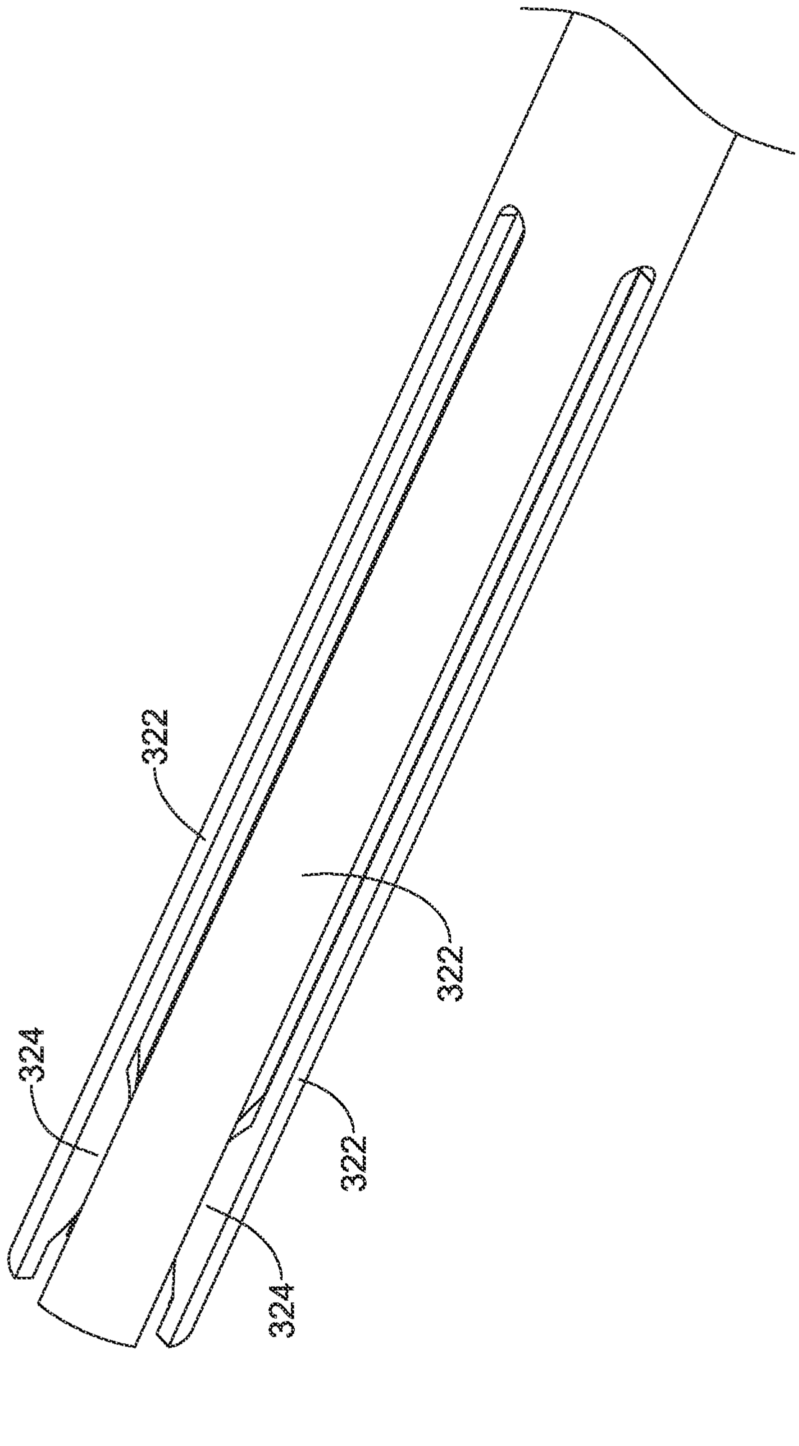
FIG. 16 is a perspective view of an inner member forming a portion of the suture translation assembly of FIG. 14 in accordance with an example of the disclosure.
Figure 17:
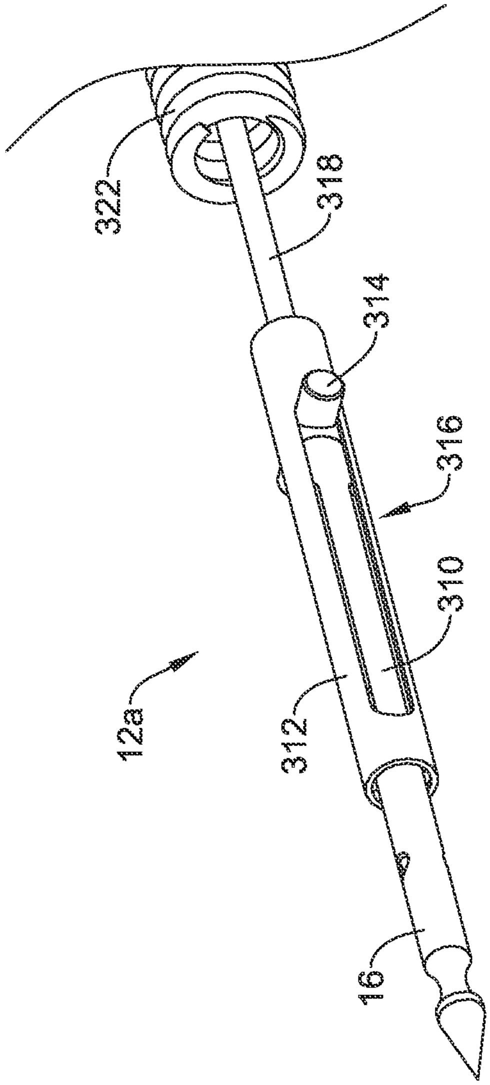
FIG. 17 is a perspective view of a portion of the suture translation assembly of FIG. 14, shown in a locked configuration in accordance with an example of the disclosure.
Figure 18:
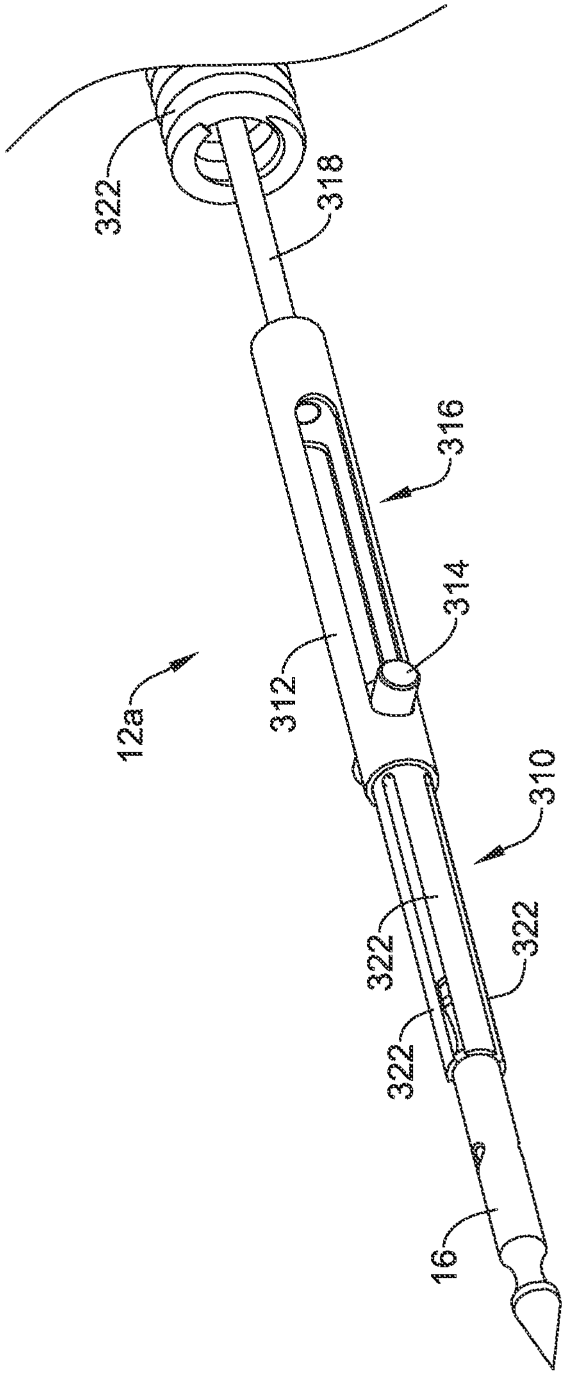
FIG. 18 is a perspective view of a portion of the suture translation assembly of FIG. 14, shown in an unlocked configuration in accordance with an example of the disclosure.

The inner member 310 includes several arms 322 that, as seen in FIG. 16, which shows the distal portion of the inner member 310, include curved tabs 324 that are configured to engage corresponding detents within the needle 16. While a total of four arms 322 are shown, it will be appreciated that the inner member 310 may include any number of arms 322. It will be appreciated that the arms 322 are relatively long in length, and as a result may be considered as being relatively flexible. With the locking member 312 extended distally into a locking configuration, as shown for example in FIG. 17, the locking member 312 prevents outward movement of the arms 322. As a result, the curved tabs 324 remain in engagement with the corresponding detents of the needle 16, and the needle 16 remains locked to the suture translation assembly 12*a*. With the locking member 312 retracted proximally into an unlocked configuration, as shown for example in FIG. 18, the arms 322 are free to move radially outwardly, thereby releasing the curved tabs 324 from the detents in the needle 16, and allowing the needle 16 to move distally relative to the inner member 310.

Figure 19:
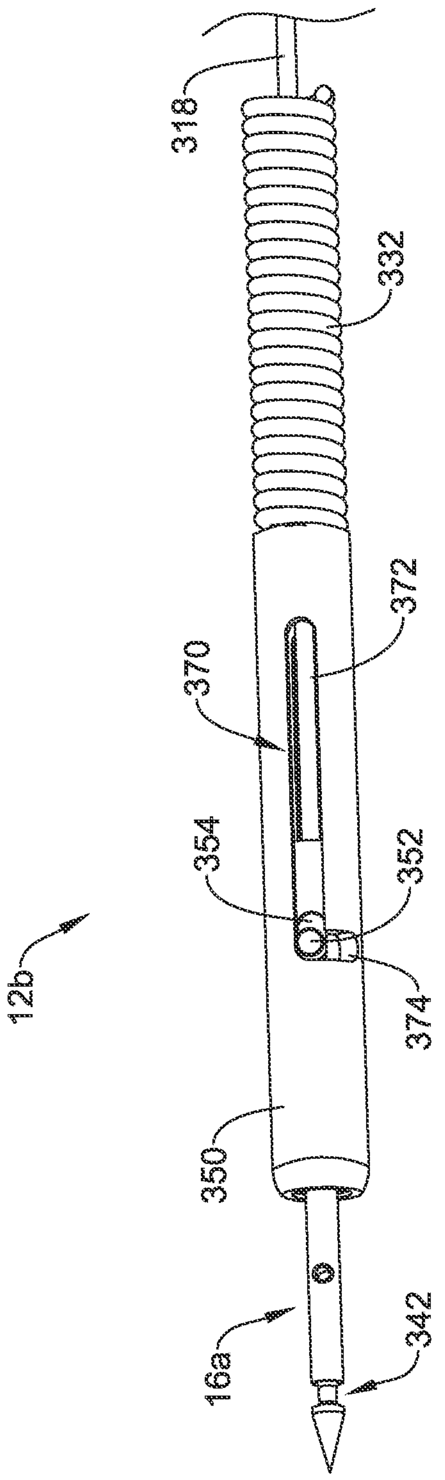
FIG. 19 is a perspective view of a suture translation assembly usable in the suture device of FIG. 1 in accordance with an example of the disclosure.
Figure 20:
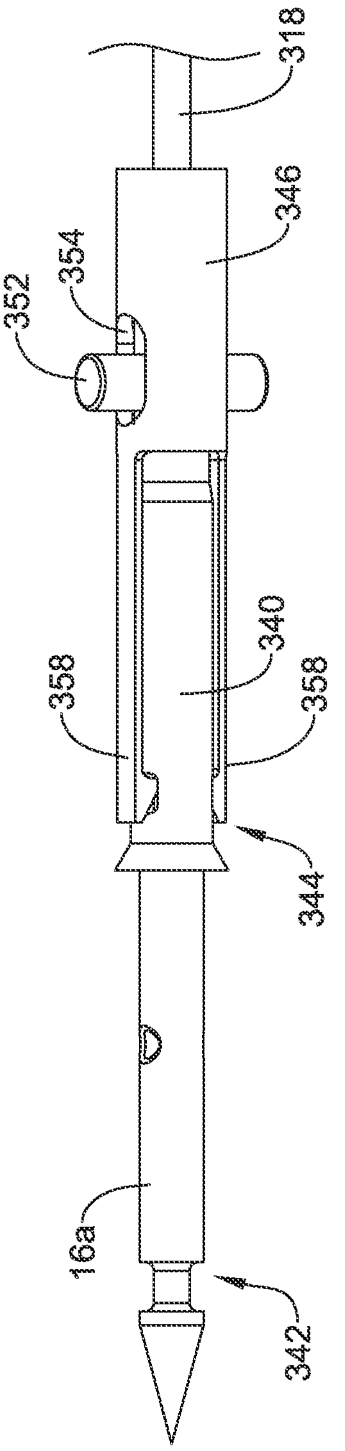
FIG. 20 is a perspective view of the suture translation assembly of FIG. 19, shown with some elements removed to show internal structure, with the suture translation assembly shown in a locked configuration in accordance with an example of the disclosure.

FIG. 19 is a perspective view of a suture translation assembly 12*b* that may be used in combination with any of the distal assembly 14, the distal assembly 14*a*, the distal assembly 14*b* and/or the distal assembly 14*c*. FIG. 20 is a perspective view of the suture translation assembly 12*b* with outer portions such as an outer sleeve 350 (FIG. 19) removed to reveal an inner member 340 that holds a needle 16*a*. In some embodiments, the outer sleeve 350 may be a single tubular member. In some instances, the outer sleeve 350 may include several elements, such as described with respect to the outer sleeve 330 (FIG. 15).

In some embodiments, as illustrated, the needle 16*a* has a distal detent 342 and a proximal detent 344 (visible in FIG. 21) that are shaped differently than the corresponding detents in the needle 16. The suture translation assembly 12*b* includes a locking member 346 that is slidingly disposable relative to the inner member 340. The pin 352 is attached to the inner member 340 and extends through a corresponding slot 354 formed in the locking member 342. The pin 352 limits translation of the locking member 342 relative to the inner member 340, and also prevents relative rotational movement of the locking member 342. The locking member 342 is secured to the control member 318, which extends distally to a handle such as the translating handle 26 (FIG. 1). As a result, the locking member 342 may be translated distally and/or proximally relative to the inner member 340.

In some embodiments, the outer sleeve 350 may define a slot 370 including an axially extending slot portion 372 and a shorter radially extending slot portion 374. In some embodiments, the axially extending slot portion 372 permits the pin 352 to move within the axially extending slot portion 372 in order to permit the needle 16*a* to be fully withdrawn into the suture translation assembly 12*b* for advancement through an endoscope or other delivery device. Once the suture translation assembly 12*b* has been advanced through the endoscope or other delivery device, the inner member 340 and the locking member 342 may be advanced distally through the outer sleeve 350 until the pin 352 aligns with the radially extending slot portion 374. By rotating the translating handle 26, the pin 352 may be rotated into position within the radially extending slot portion 374 so that the locking member 342 may be translated relative to the inner member 340.

Figure 21:
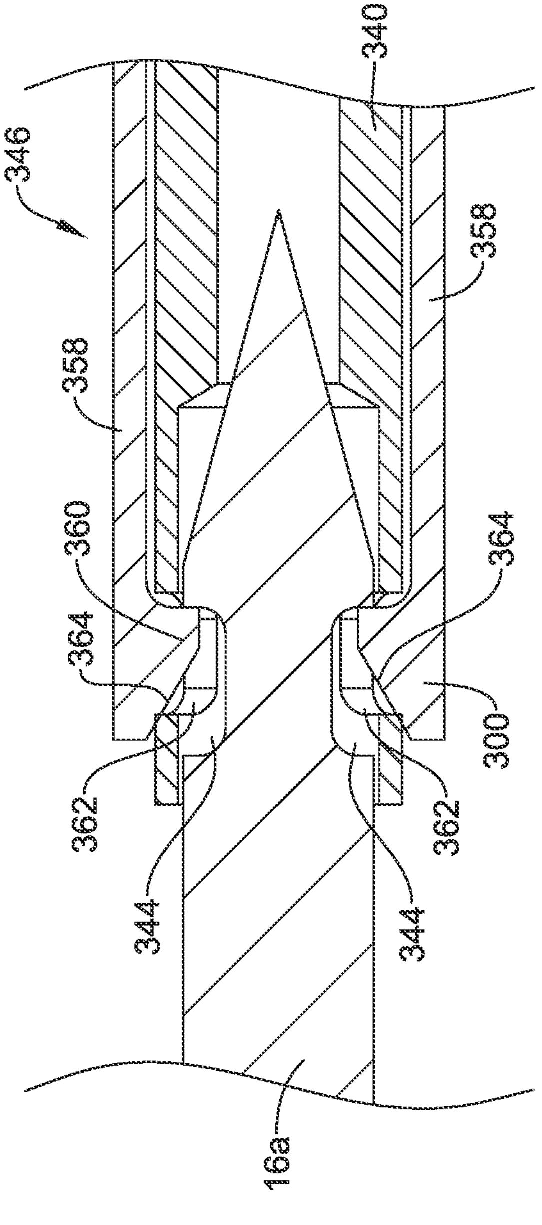
FIG. 21 is a side view of a portion of the suture translation assembly of FIG. 19, showing how a locking member engages an inner member of the suture translation assembly and a needle in the locked configuration as shown in FIG. 20 and in accordance with an example of the disclosure.

In some embodiments, as illustrated, the locking member 342 includes a pair of arms 358 that extend distally from the locking member 342. As seen for example in FIG. 21, the arms 358 include tabs 360 that, when the suture translation assembly 12*b* is in a locked configuration as shown in FIGS. 20 and 21, the tabs 360 extend through slots 362 formed within the inner member 340. As a result, the tabs 360 are able to extend through the slots 362 and engage the proximal detent 344 of the needle 16*a*. While a pair of arms 358 are illustrated, it will be appreciated that the locking member 342 may include any number of arms 358, and of course a corresponding number of slots 362.

Figure 22:
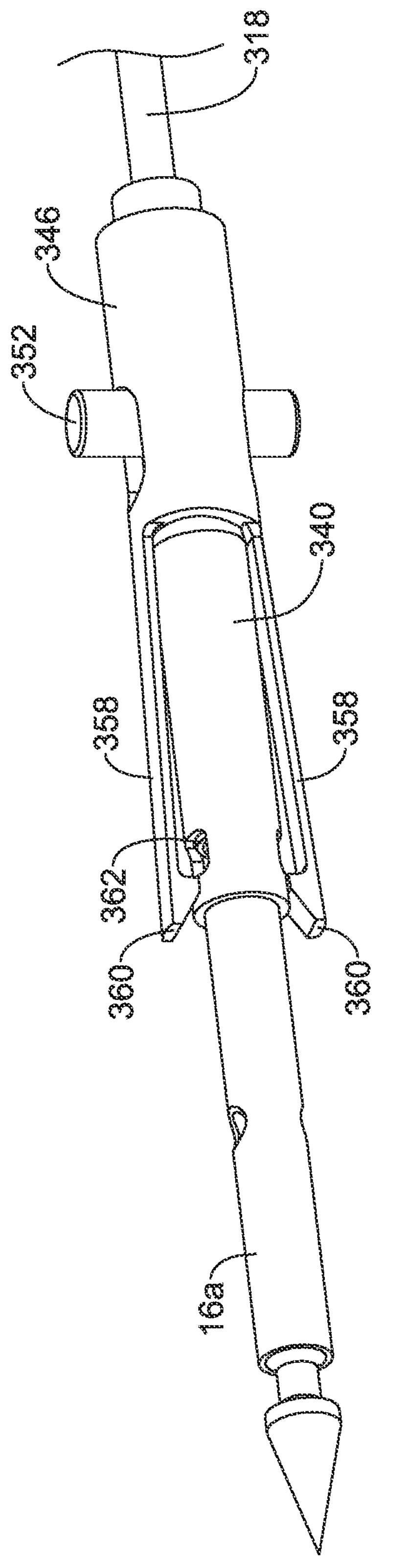
FIG. 22 is a perspective view of the suture translation assembly of FIG. 19, shown in an unlocked configuration in accordance with an example of the disclosure.

In order to move the suture translation assembly 12*b* into an unlocked configuration, as shown for example in FIG. 22, the locking member 342 may be moved distally relative to the inner member 340. As can be seen in FIG. 22, the tabs 360 have moved out of the slots 362 (only one slot 362 is seen), and the needle 16*a* is free to move relative to the suture translation assembly 12*b*. As the locking member 342 moves distally, angled surfaces 364 push against the slots 362 and are moved outwardly.

In some embodiments, and with respect to FIG. 13, the guide member 36*a* includes a channel 300 that is configured to permit a suture to pass between the suture translation assembly 12, 12*a*, 12*b* and a working channel of the endoscope or other delivery device to which the distal assembly 14*c* is attached. The channel 300 may, for example, be designed to include a lead in that would help to align the suture with the channel 300 when passing the suture translation assembly 12, 12*a*, 12*b* through the working channel of the endoscope or other delivery device. In some embodiments, there may be a desire to load the suture before passing the suture translation assembly 12, 12*a*, 12*b* through the working channel of the endoscope or other delivery device.

Figure 23:
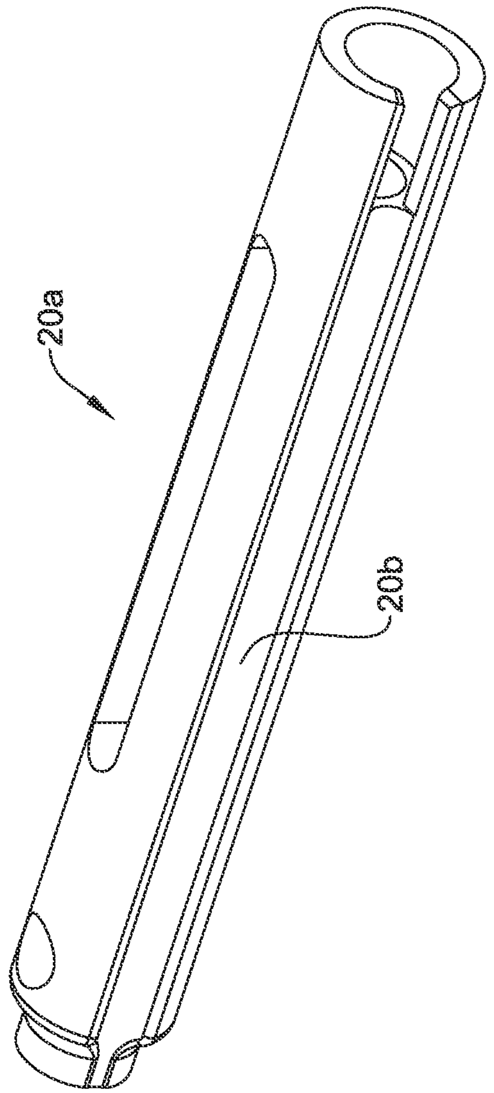
FIG. 23 is a perspective view of a sleeve usable as part of a suture translation assembly.
Figure 24:
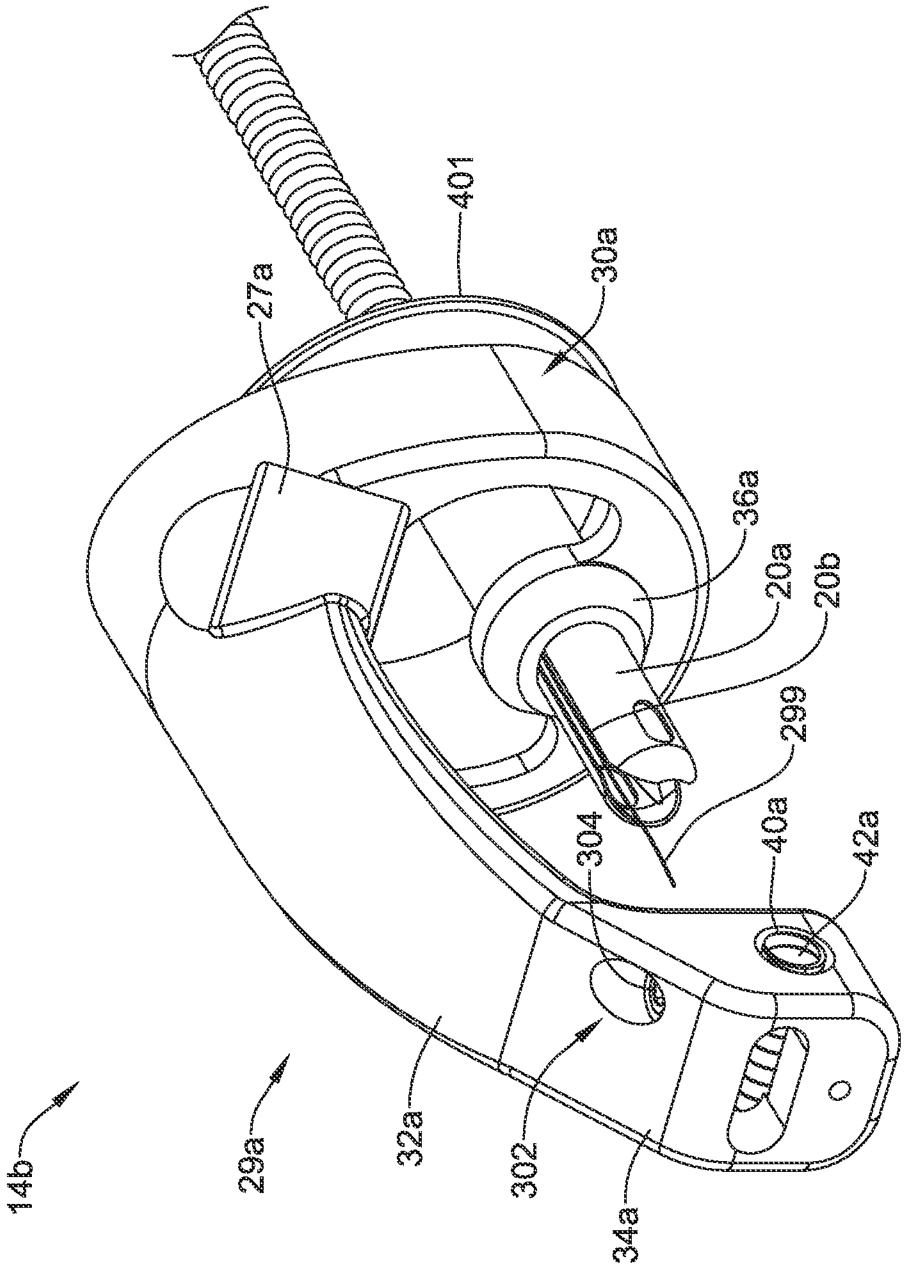
FIG. 24 is a perspective view of a distal assembly utilizing the sleeve of FIG. 23 and usable in the suture device of FIG. 1 in accordance with an example of the disclosure.

In some instances, as shown for example in FIG. 23, instead of putting a channel 300 in the guide member 36*a*, the suture translation assembly 12, 12*a*, 12*b* may be modified to accommodate a suture passing along the suture translation assembly 12, 12*a*, 12*b*. FIG. 23 is a perspective view of a sleeve 20*a* that may be used in forming a part of the suture translation assembly 12, 12*a*, 12*b*. It can be seen that the sleeve 20*a* includes a groove 20*b* that extends a length of the sleeve 20*a*. FIG. 24 shows the sleeve 20*a* extending through the guide member 36*a*, with a suture 299 extending through the groove 20*b*.

In some embodiments, there may be a desire to protect the distal end of the needle 16 when advancing the suture translation assembly 12, 12*a*, 12*b* through a delivery system such as an endoscope. In some embodiments, the needle 16 may otherwise be able to damage a working channel with the endoscope, for example. In some instances, there may be a desire to protect the needle 16 itself from becoming damaged. In some embodiments, the sleeve 20, 20*a* covering the needle 16 and the distal shuttle 18 (FIGS. 1-5) may be dislodged proximally during loading, resulting in possible exposure of the needle 16. In some embodiments, it may be difficult to load through a bend in the working channel of the endoscope when the sleeve 20, 20*a* is extended over the needle 16.

Figure 25:
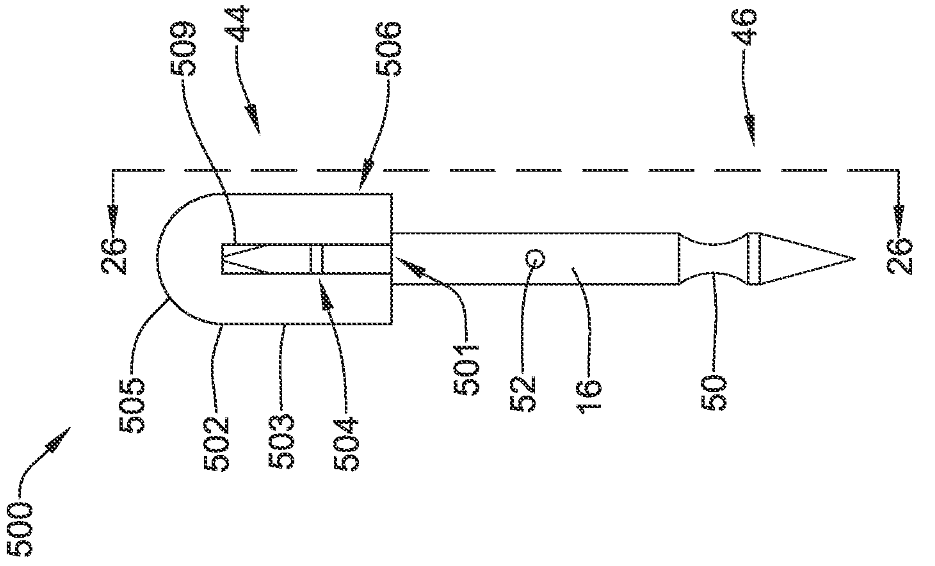
FIG. 25 is a view of a needle bearing a needle cap in accordance with an example of the disclosure.
Figure 26:
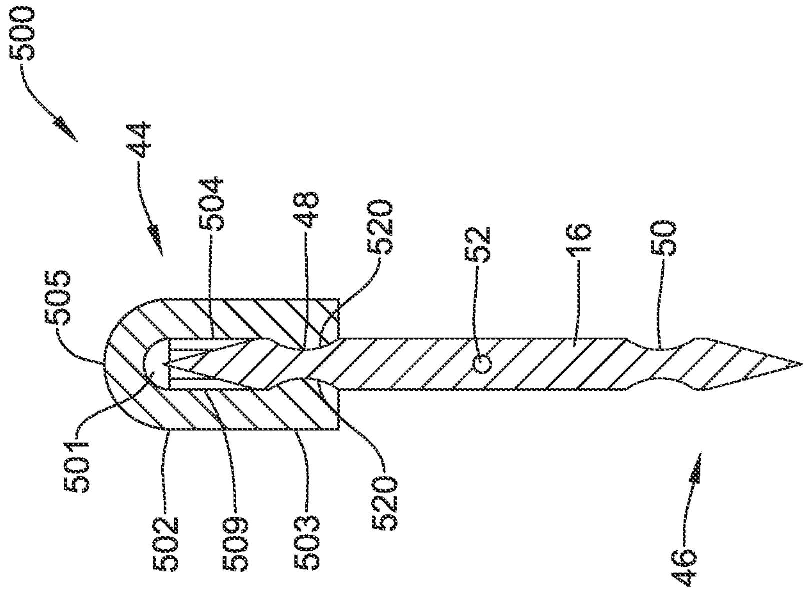
FIG. 26 is a cross-sectional view of the needle and needle cap of FIG. 25, taken along the line 26-26.

FIGS. 25 and 26 illustrate an example in which a needle cap 500 has been placed over the distal region 44 of the needle 16. FIG. 25 is a side view while FIG. 26 is a cross-sectional view taken along line 26-26 of FIG. 25. In some embodiments, the needle cap 500 may be removed outside of the patient, after the suture translation assembly 12, 12*a*, 12*b* has been loaded into the endoscope but before the endoscope has been inserted into the patient. In some embodiments, the needle cap 500 may be pushed off of the needle 16 inside the patient. When performing a procedure utilizing multiple needles and sutures, such as but not limited to endoscopic sleeve gastroplasty, it may be desirable to remove the needle cap 500 with the endoscope inside the patient so that the endoscope does not have to be removed and inserted multiple times. In some embodiments, the needle cap 500 can be pushed off of the needle 16 by moving the sleeve 20, 20*a* distally. In some embodiments, the needle cap 500 may be configured to split when the needle cap 500 contacts the distal endcap 14, 14*a*, 14*b*, 14*c*.

The needle cap 500 includes a cylindrical needle cap body 503 that defines a void 501 that is configured to fit over the needle 16. The needle cap 500 also includes an atraumatic tip 505 that is integrally molded with or otherwise attached to the cylindrical needle cap body 503. In some embodiments, the needle cap 500 includes one or more elongate slots 509 that extend axially along the cylindrical needle cap body 503 and provide sufficient flexibility to allow the needle cap 500 to flex enough to be advanced onto the needle 16. In some embodiments, there may be two slots 509, although only one is visible in FIGS. 25 and 26. The needle cap 500 includes one or more convex protuberances 520 that are configured to fit into the distal detent 48 of the needle 16.

Figure 27:
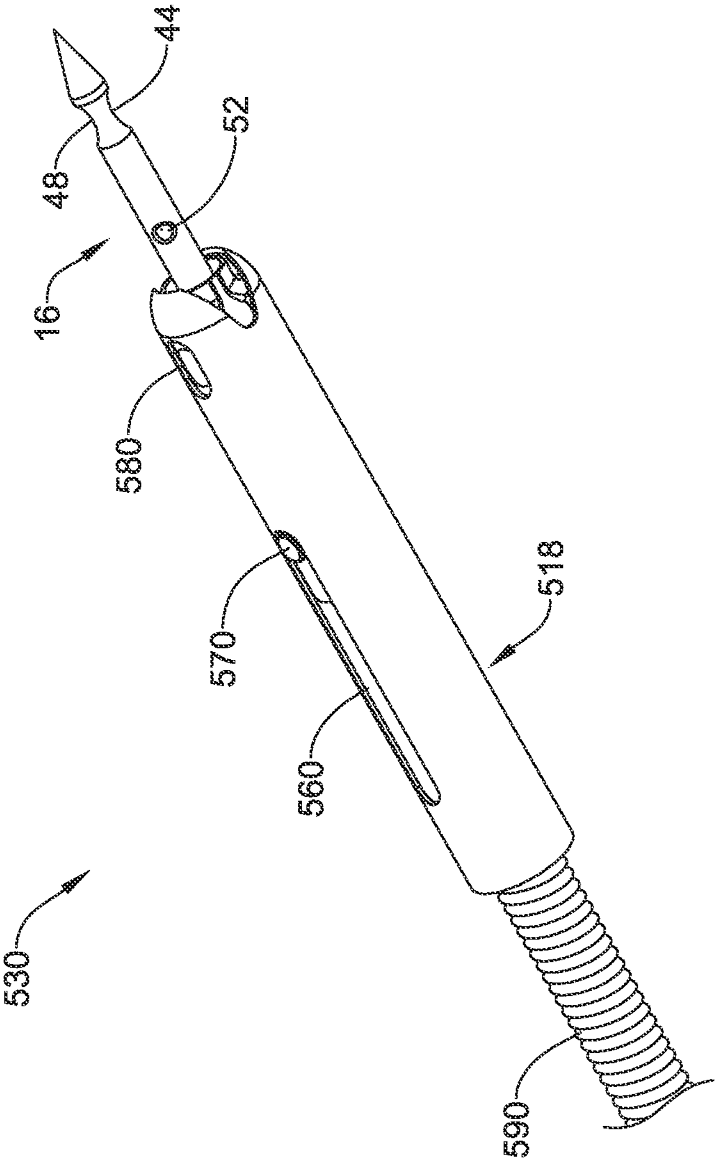
FIG. 27 is a perspective view of a suture translation assembly with a needle shown in an unlocked position in accordance with an example of the disclosure.
Figure 28:
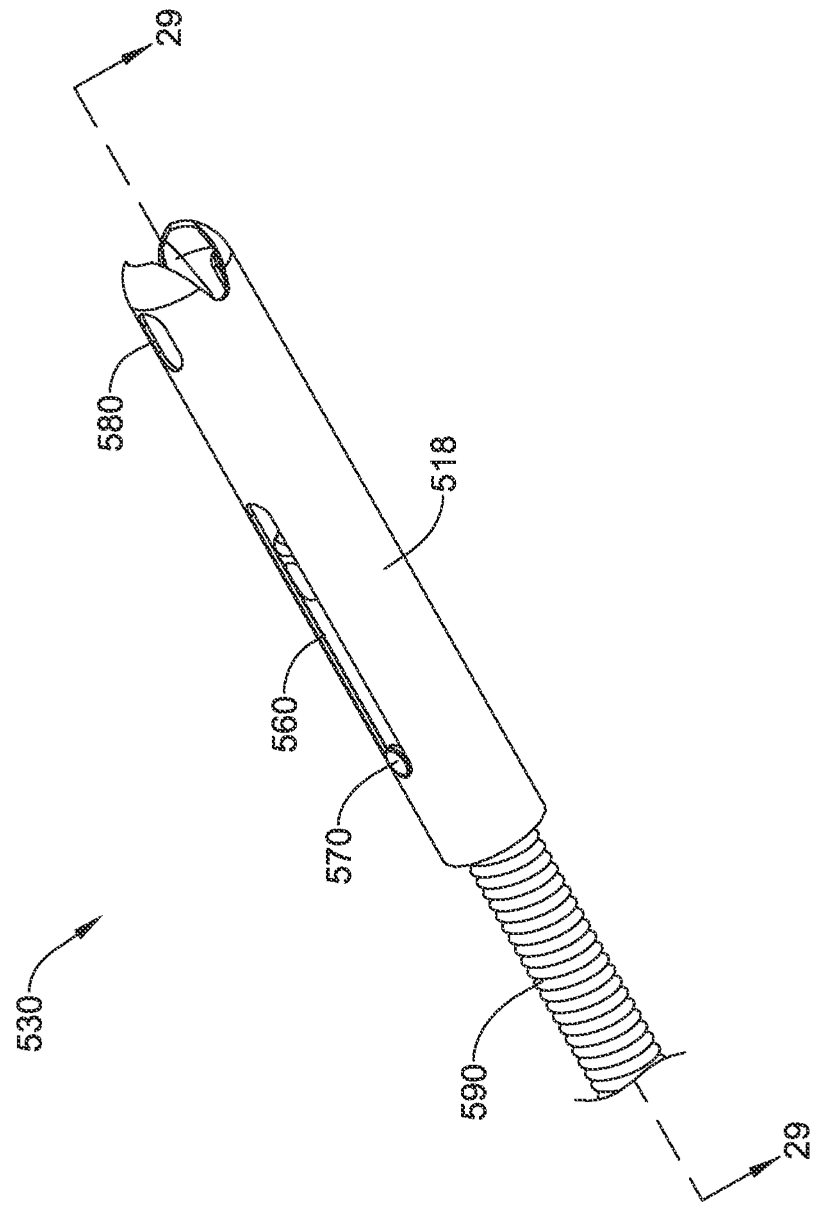
FIG. 28 is a perspective view of the suture translation assembly of FIG. 27, with the needle shown in a locked position in accordance with an example of the disclosure.

FIGS. 27 through 30 illustrate another way of protecting the needle 16, either from damaging the interior of an endoscope or from becoming damaged itself. FIGS. 27 through 30 are various views of a suture translation assembly 530 that provides a reduced overall length that facilitates loading into an endoscope. In some instances, the suture translation assembly 530 is short enough to permit easy passage through an endoscope with the sleeve in place over the needle. In some embodiments, control of the suture translation assembly 530 is reversed relative to the suture translation assemblies 12, 12*a*, 12*b* described with respect to previous Figures. FIG. 27 shows the suture translation assembly 530 in an unlocked position, in which the needle 16 is unlocked relative to the distal shuttle and can be passed to the distal endcap 14, 14*a*, 14*b*, 14*c*. FIG. 28 shows the suture translation assembly 530 in a locked position, in which the needle 16 is locked to the distal shuttle. As seen, the suture translation assembly 530 includes a sleeve 518 and a suture catheter 590. In some embodiments, as illustrated, the suture catheter 590 is a coil. The sleeve 518 has a pair of slots 560 (only one slot 560 is visible in the illustrated orientation) in order to accommodate movement of a distal shuttle, as will be discussed. The sleeve 518 also includes a pair of sleeve openings 580 (only one visible) that permit bearing balls 58 (not shown) to move in and out relative to a distal shuttle, thereby locking and unlocking the needle 16.

Figure 29:
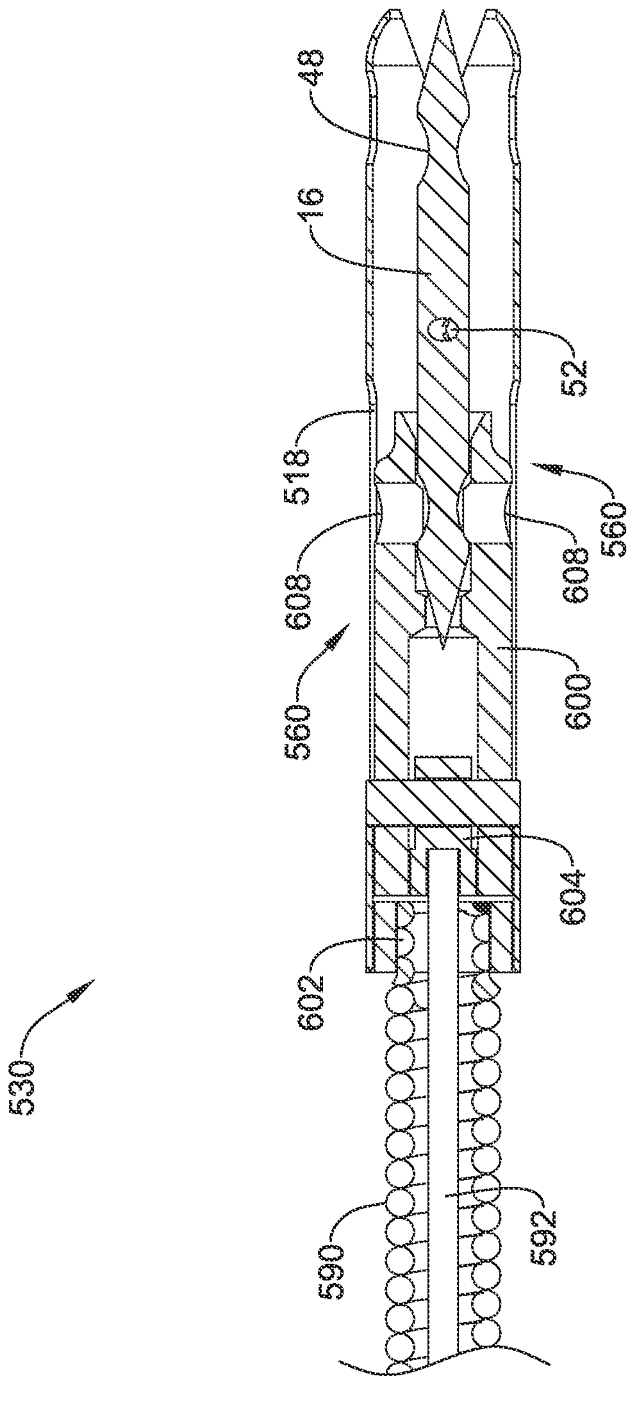
FIG. 29 is a cross-sectional view of the suture translation assembly of FIG. 28, taken along the line 29-29.
Figure 30:
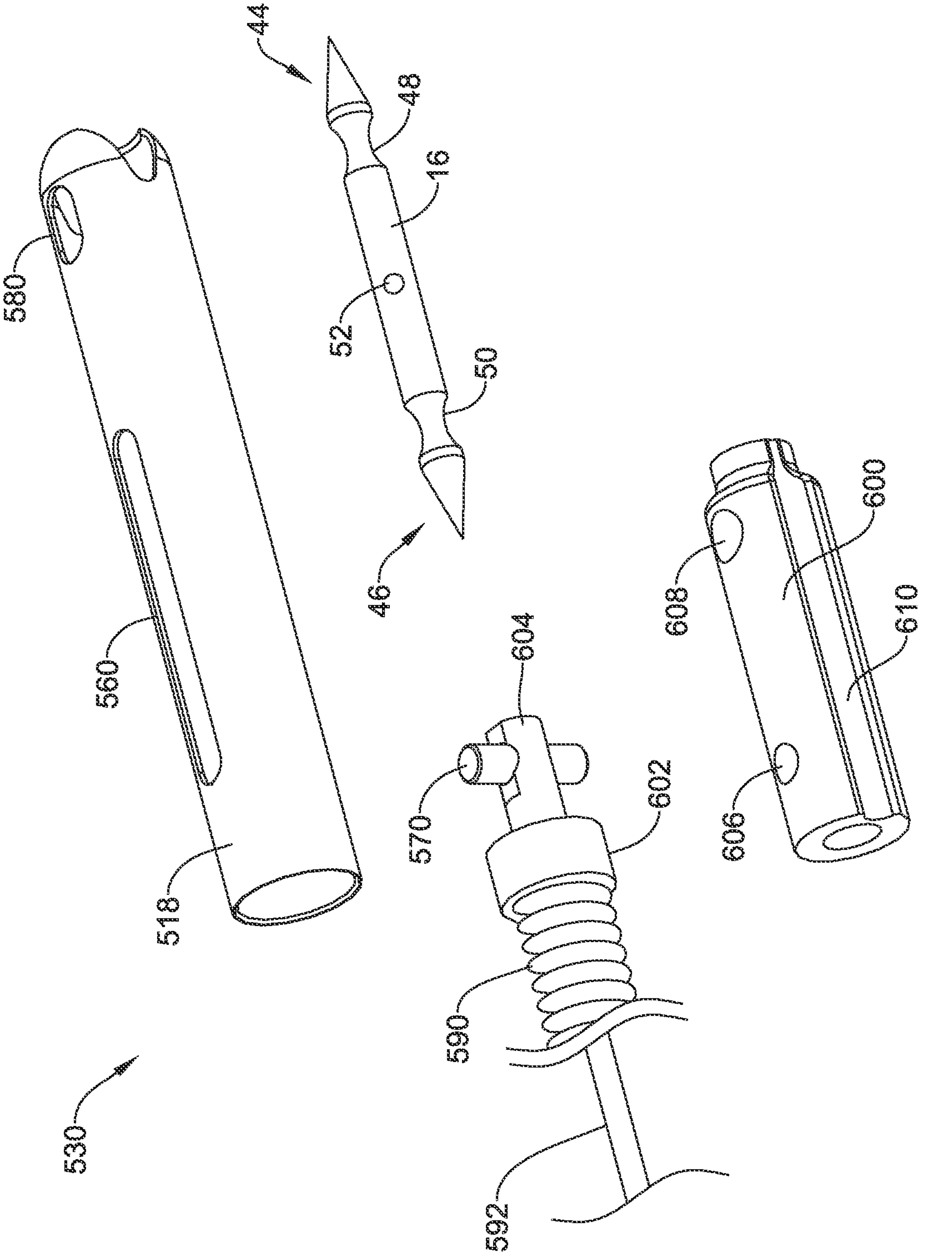
FIG. 30 is a partial exploded view of the suture translation assembly of FIG. 28.

The internal structure of the suture translation assembly 530 is better seen in FIG. 29, which is a cross-sectional view taken along the line 29-29 of FIG. 28, as well as FIG. 30, which is a partially exploded view of FIG. 28. As can be seen, a control wire 592 extends through the suture catheter 590 and terminates within a yoke 604. The sleeve 518 is coupled to the suture catheter 590 via a coupler 602. In some embodiments, the sleeve 518 may be welded to the suture catheter 590, either directly or by being welded to the coupler 602. As a result, the sleeve 518 does not move relative to the suture catheter 590.

A pin 570 extends through the yoke 602 and into apertures 606 that are formed within a distal shuttle 600, thereby operably coupling the control wire 592 to the distal shuttle 600. The pin 570 extends to and is guided by a pair of slots 560 that are formed in the sleeve 518. This prevents rotation of the distal shuttle 600 relative to the sleeve 518. In some embodiments, the distal shuttle 600 includes a groove 610 that allows a suture to extend from the needle 16 and extend axially through the sleeve 518.

The distal shuttle 600 also includes a pair of bearing ball openings 608. As discussed previously, when the bearing ball openings 608 are aligned with the sleeve openings 580, the bearing balls 58 (not shown) are free to move radially outwardly sufficiently to clear the proximal detent 50 of the needle 16, thereby unlocking the needle 16 from the distal shuttle 600. Conversely, when the bearing ball openings 608 are misaligned with the sleeve openings 580, the bearing balls 58 (not shown) are not able to clear the proximal detent 50 of the needle 16, and the needle 16 remains locked to the distal shuttle 600. Accordingly, moving the control wire 592 in a proximal direction moves the distal shuttle 600 in a proximal direction relative to the sleeve 518. This causes the sleeve openings 580 to misalign with the bearing ball openings 608 and locks the needle 16 to the sleeve 518. Conversely, moving the control wire 592 in a distal direction moves the distal shuttle 600 in a distal direction relative to the sleeve 518.

Figure 31:
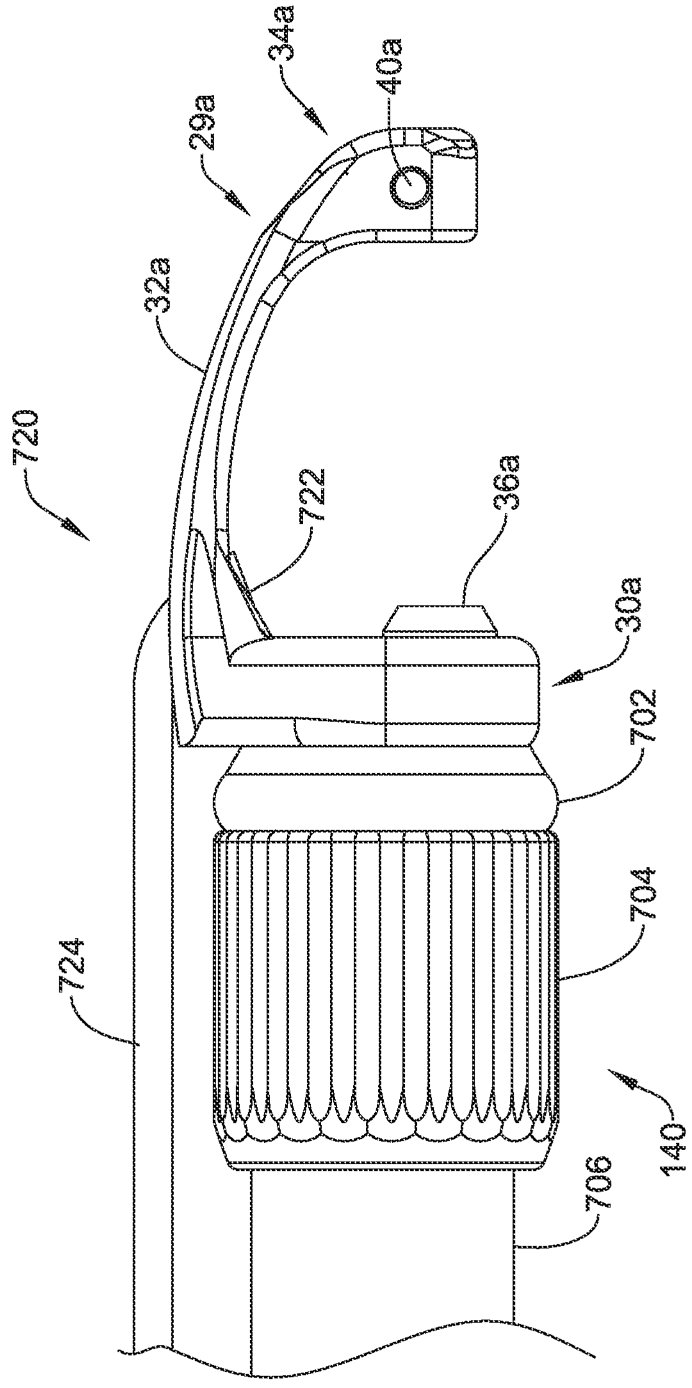
FIG. 31 is a perspective view of a distal assembly including an elongate tool guide in a deployment configuration, the distal assembly usable in the suture device of FIG. 1 in accordance with an example of the disclosure.
Figure 32:
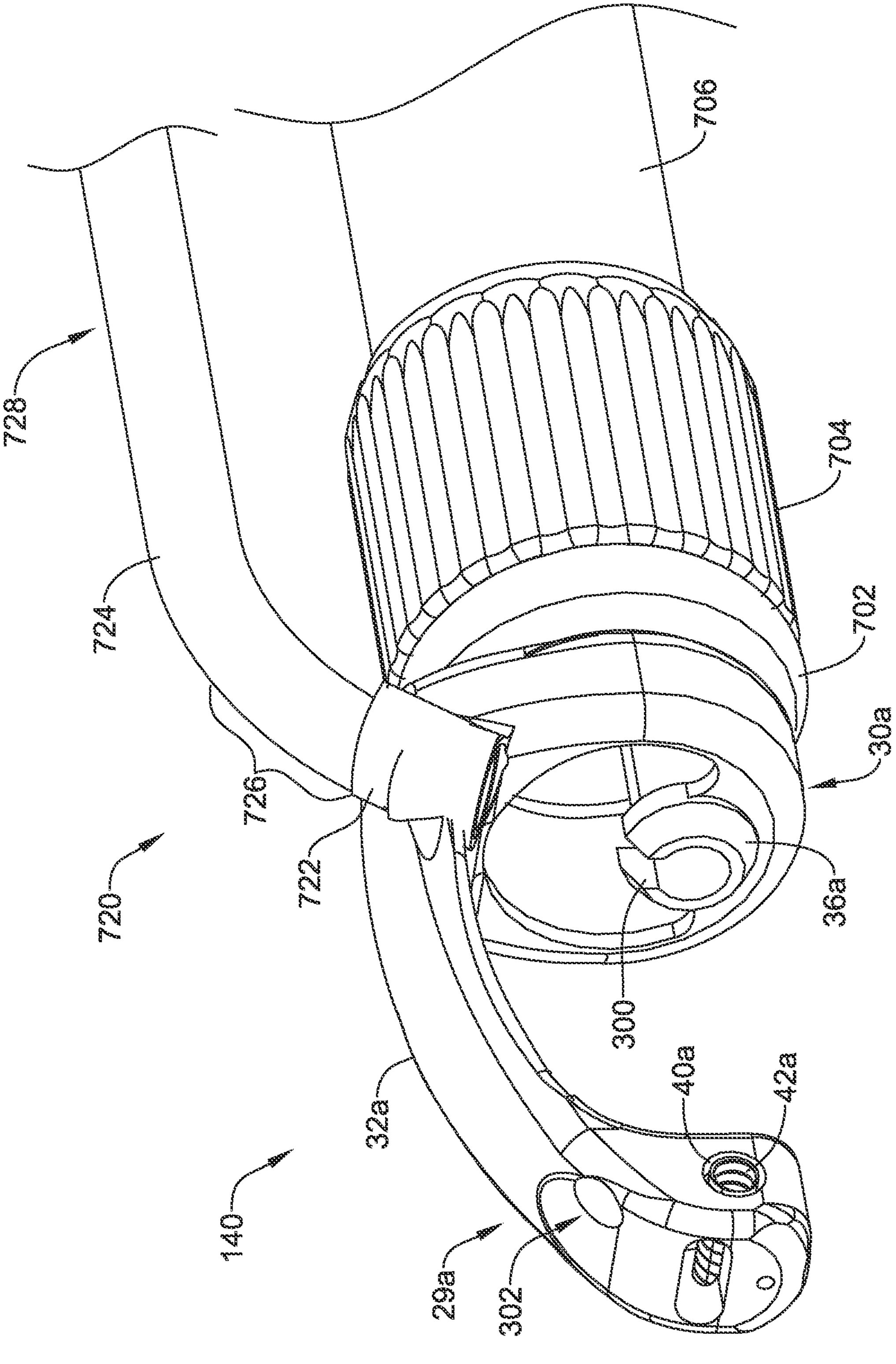
FIG. 32 is a perspective view of a distal assembly including an elongate tool guide in a working configuration, the distal assembly usable in the suture device of FIG. 1 in accordance with an example of the disclosure.

FIGS. 31 and 32 are perspective views of a distal assembly 14*d* that may, for example, be usable in the suture device 10 shown in FIG. 1. FIG. 31 shows the distal assembly 14*d* with an elongate tool guide 720 in a deployment configuration while FIG. 32 shows the distal assembly 14*d* with the elongate tool guide 722 in a working configuration. It will be appreciated that in the deployment configuration, the distal assembly 14*d* is more compact, as features of the elongate tool guide 720 are closer to the distal assembly 14*d*. The distal assembly 14*d* is similar to the distal assembly 14 shown in previous Figures, but includes modifications that aid both in delivery of the distal assembly 14*d* as well as subsequently providing tools to a working site.

The distal assembly 14*d* may include a body 29*a* having a proximal connector 30*a* that may be configured to be coupled to the distal end of an endoscope or other delivery system, for example. In some embodiments, as illustrated, the proximal connector 30*a* may include an inner collet adaptor 702 that engages a fixation feature 401 (not visible in this drawing) and an outer collet adaptor 704 that threadedly engages the inner collet adaptor 702. Together, the inner collet adaptor 702 and the outer collet adaptor 704 may be used to secure the distal assembly 14*d* to an endoscope body 706. The body 29*a* includes an arm 32*a* that extends to an endcap 34*a*. In some embodiments, the body 29*a*, including the arm 32*a*, may be similar to the body 29 and arm 32 referenced previously with respect to the distal assembly 14, the distal assembly 14*a*, the distal assembly 14*b* and the distal assembly 14*c*. The distal assembly 14*d* may be considered as including a guide member 36*a* that may be secured to or integrally formed with the body 29*a*, and may be configured to permit a suture translation assembly (such as the suture translation assembly 12, a suture translation assembly 12*a*, shown in FIG. 14 through FIG. 18, or a suture translation assembly 12*b*, shown in FIG. 19 through FIG. 22) to extend through the guide member 36*a* and to translate relative to the guide member 36*a*.

In some embodiments, as illustrated in FIG. 32, the guide member 36*a* includes a channel 300. In some embodiments, the channel 300 permits a suture to pass between the suture translation assembly 12, 12*a*, 12*b* and a working channel of the endoscope or other delivery device to which the distal assembly 14*d* is attached. The channel 300 may, for example, be designed to include a lead in that would help to align the suture with the channel 300 when passing the suture translation assembly 12, 12*a*, 12*b* through the working channel of the endoscope or other delivery device. In some embodiments, there may be a desire to load the suture before passing the suture translation assembly 12, 12*a*, 12*b* through the working channel of the endoscope or other delivery device.

The end cap 34*a* includes one or more securement openings 40*a* that may be, as can be seen, be arranged orthogonally to a proximal needle opening (not illustrated), such as the proximal needle opening 37 illustrated for example in FIG. 3. One or more securements 42*a* may correspondingly be disposed within the one or more securement openings 40*a*. In some embodiments, the one or more securements 42*a* may be a coil spring that is disposed within the one or more securement openings 40*a*. The securement 42*a* may releasably engage a detent on the needle 16, as discussed with respect to the distal assembly 14.

In some embodiments, the securement opening 40*a* may have a diameter that is greater than an overall diameter of the securement 42*a* and the securement opening 40*a* may taper to a diameter on an opposing side (not seen) that is about the same as the diameter of the securement 42*a*. In some embodiments, the securement 42*a* may be welded, soldered, adhesively secured or otherwise attached at the left side of the securement opening 40*a*, and may be free to move somewhat at the right side of the securement opening 40*a*. In some instances, the distal assembly 14*c* may include an opening 302 that is orthogonal to the securement opening 40*a*. The opening 302 may be threaded in order to threadedly engage a set screw 304. In some embodiments, as illustrated, the opening 302 may be offset closer to the right side of the securement opening 40*a*, away from the secured end of the securement 42*a*, such that the set screw 304 may be considered as supporting the free end of the securement 42*a*. Rotating the set screw 304 in a first direction, such as clockwise, may cause the set screw 304 to translate towards the securement 42*a*, thereby increasing an interference between the securement 42*a* and the needle 16 and increasing a retentive force that can be applied to the needle 16. Conversely, rotating the set screw in a second direction, such as counter-clockwise, may cause the set screw 304 to translate away from the securement 42*a*, thereby decreasing the retentive force that can be applied to the needle 16. This may help to adjust for manufacturing tolerances, for example As noted above, in some instances, the distal assembly 14*d* includes an elongate tool guide 720. The elongate tool guide 720 may take a variety of forms. As shown in FIGS. 31 and 32, the elongate tool guide 720 includes a guide structure 722 that is attached to or integrally formed with the body 29*a*. A polymeric tubular member 724 is secured to and extends through the guide structure 722. The polymeric tubular member 724 extends proximally from the distal assembly 14*d* such that various tools may be advanced through the polymeric tubular member 724 and thus reach a working site that may be considered as a region between the guide member 36*a* and the endcap 34*a*. In FIG. 31, the polymeric tubular member 724 may be seen as being collapsed down against the distal assembly 14*d* in a deployment configuration that minimizes the overall dimensions of the distal assembly 14*d*. In FIG. 32, the polymeric tubular member 724 may be seen as being in a working configuration in which the polymeric tubular member 724 curves away from the distal assembly 14*d*.

In some instances, the polymeric tubular member 724 may include a distal region 726 and a proximal region 728. In some cases, the distal region 726 may be formed of a polymer having a relatively lower durometer, meaning that the distal region 726 is more flexible, while the proximal region 728 may be formed of a polymer having a relatively higher durometer, meaning that the proximal region 728 is less flexible. This may assist the polymeric tubular member 724 in moving between the deployment configuration and the working configuration. The distal region 726 and the proximal region 728 may be formed of two different polymers, or the same polymer with differing durometers. In some cases, while described as being polymeric, it is possible that the polymeric tubular member 724 may instead be formed of a metallic material. It is contemplated that the polymeric tubular member 724 may move from being collapsed down against the distal assembly 14*d* by virtue of extending a tool distally through the polymeric tubular member 724.

Figure 33:
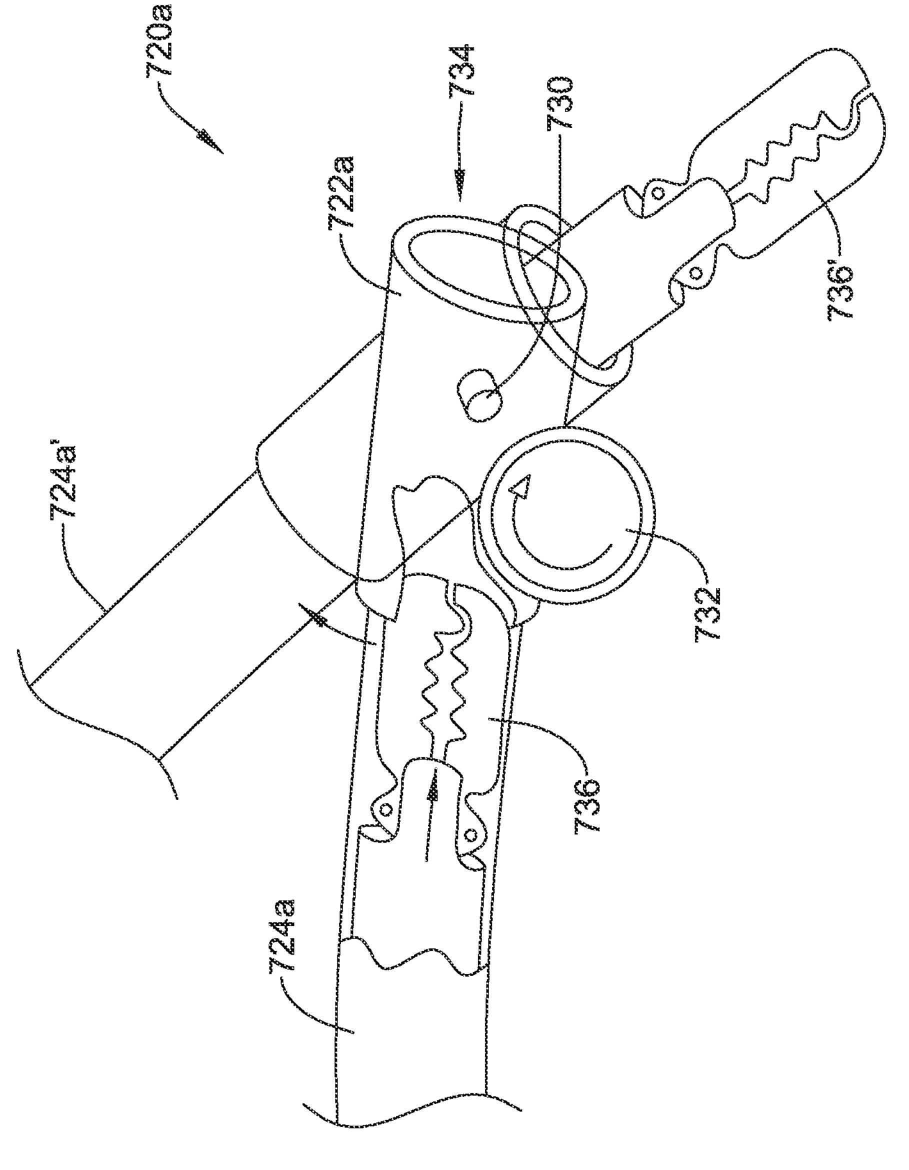
FIG. 33 is a partial cross-sectional perspective view of an elongate tool guide usable in the suture device of FIG. 1 in accordance with an example of the disclosure.

FIG. 33 is a schematic view of an elongate tool guide 720*a* that may be used. The elongate tool guide 720*a* includes a guide structure 722*a* that is pivotably secured relative to the distal assembly (not shown in this Figure) via a pivot point 730. The elongate tool guide 720*a* also includes a polymeric tubular member 724*a* that is secured to and extends through the guide structure 722*a*. The elongate tool guide 720*a* includes a pivot structure 732. The pivot structure 732 may be a ball, a ramp or other shape that extends at least partially into a lumen 734 extending through the guide structure 722*a*. As a result, when a tool 736 (illustrated as a forceps) extends distally through the polymeric tubular member 724*a*, continued distal pressure applied by the tool 736 will cause the guide structure 722*a* to rotate about the pivot point 730. As a result, the elongate tool guide 720*a* may rotate from the deployment configuration to the working configuration, where the polymeric tubular member is labeled as 724*a*' and the tool is labeled as 736'. By comparing FIG. 33 to FIG. 32, it will be appreciated that in the working configuration, the tool 736' is positioned to readily access the aforementioned working site.

Figure 34:
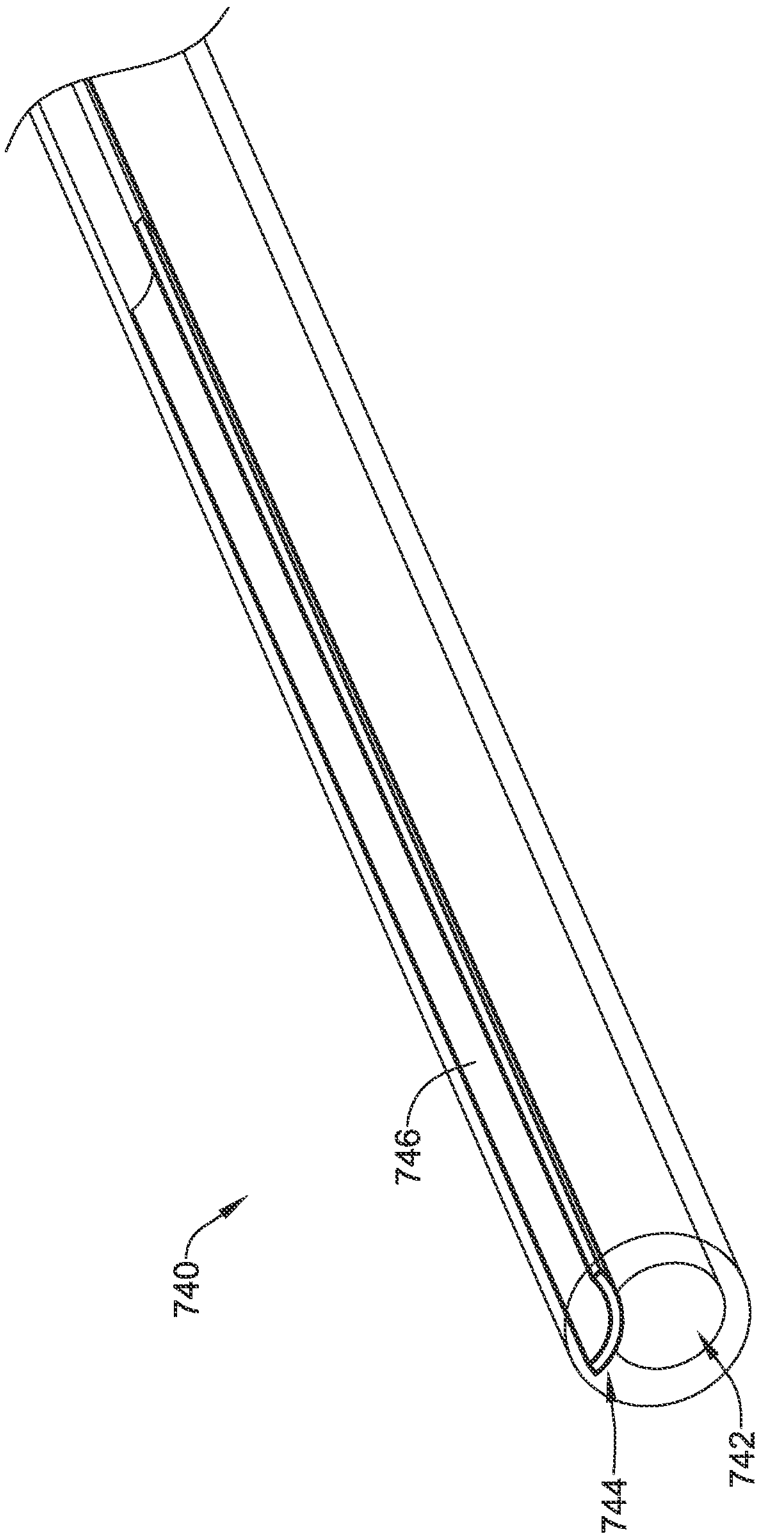
FIG. 34 is a perspective view of a portion of an elongate tool guide shown in a deployment configuration, the elongate tool guide usable in the suture device of FIG. 1 in accordance with an example of the disclosure.
Figure 35:
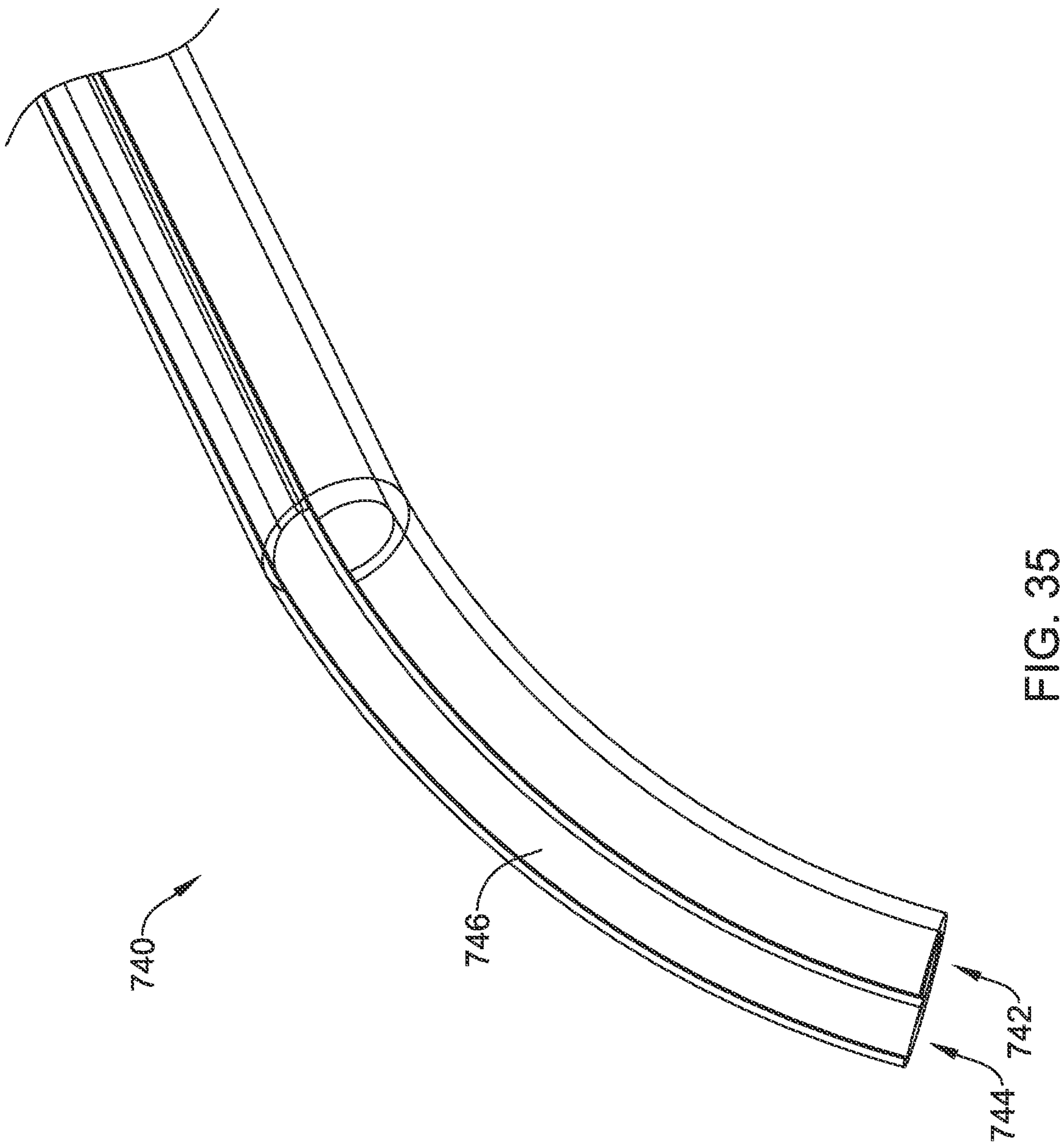
FIG. 35 is a perspective view of a portion of an elongate tool guide shown in a working configuration, the elongate tool guide usable in the suture device of FIG. 1 in accordance with an example of the disclosure.

FIGS. 34 and 35 are perspective views of a tubular member 740 that may be used as part of an elongate tool guide. The tubular member 740 includes at least a first lumen 742 and a second lumen 744. The first lumen 742 may be considered as being configured to accommodate a tool therethrough, such as but not limited to a forceps as shown in FIG. 33. The second lumen 744 may be considered as being configured to accommodate an elongate member 746 extending through the second lumen 744. In some cases, the elongate member 746 may be used to control movement between a deployment configuration as shown in FIG. 34 and a working configuration as shown in FIG. 35.

In some cases, the elongate member 746 may be a ribbon made of a metallic or polymeric shape-memory material that has an original configuration (such as linear) and a remembered configuration (such as curved). It will be appreciated that an elongate tool guide formed using the tubular member 740 may begin in the deployment configuration in which the elongate member 746 is in a linear configuration. Before extending a tool distally through the tubular member 740, the elongate member 746 may be actuated into its remembered configuration by, for example, applying an electrical current to the elongate member 746. In some cases, the elongate member 746 may not be inserted into the second lumen 744 until it is time to cause the tubular member 740 to move from the deployment configuration to the working configuration.

In some cases, the elongate member 746 may be a bi-stable material, having a stable linear configuration. When delivering a tool through the first lumen 742, the act of the tool striking a side wall of the elongate member 746, and hence applying a small force to the elongate member 746, may cause the elongate member 746 to revert to its unstable, curved, configuration.

Figure 36C:
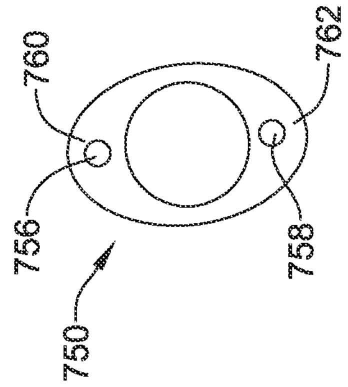
FIG. 36C is a cross-sectional view of the portion of the elongate tool guide of FIG. 36B, taken along line 36-36.
Figure 36A:
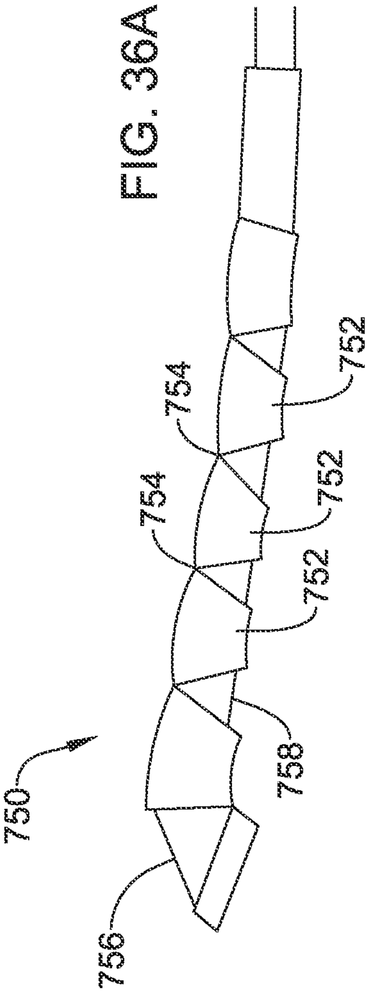
FIG. 36A is a side view of a portion of an elongate tool guide shown in a deployment configuration, the elongate tool guide usable in the suture device of FIG. 1 in accordance with an example of the disclosure.
Figure 36B:
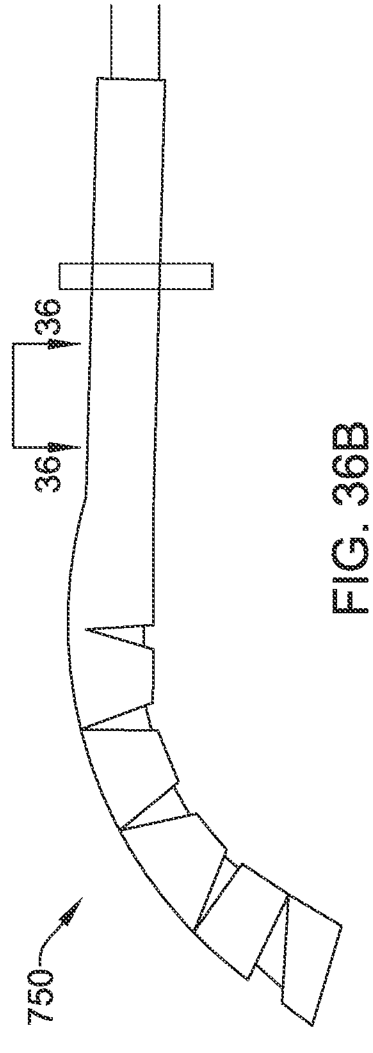
FIG. 36B is a side view of a portion of the elongate tool guide shown in a working configuration, the elongate tool guide usable in the suture device of FIG. 1 in accordance with an example of the disclosure.

FIGS. 36A, 36B and 36C illustrate a tubular member 750 that may be used as part of an elongate tool guide. FIG. 36A shows the tubular member 750 in the deployment configuration while FIG. 36B shows the tubular member 750 in the working configuration. As can be seen, the tubular member 750 is formed of a number of conduit segments 752 that are each joined together via living hinges 754. It will be appreciated that each living hinge 754 is a hinge formed from a flexible portion of the material forming the two conduit segments 752 on either side of the living hinge 754. As illustrated, a first cable 756 and a second cable 758 each extend through each of the conduit segments 752. As shown in FIG. 36C, which is a cross-sectional view taken along line 36-36 of FIG. 36B, each conduit segment 752 includes a first cable aperture 760 and a second cable aperture 762, with the first cable 756 extending through the first cable aperture 756 and the second cable 758 extending through the second cable aperture 762. It will be appreciated that by applying appropriate forces to the first cable 756 and/or the second cable 758, the tubular member 750 may be caused to move from the deployment configuration shown in FIG. 36A to the working configuration shown in FIG. 36B. In some cases, the tubular member 750 may only include a single cable, such as the second cable 758.

It will be appreciated that a variety of different materials may be used in forming the devices described herein. In some embodiments, a variety of different metals may be used. Illustrative but non-limiting examples of suitable metals include titanium, stainless steel, magnesium, cobalt chromium and others. In some embodiments, for example, the devices described herein may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A medical device, comprising:
- a delivery system including a lumen extending through the delivery system; and
- an elongate tool guide extending along and pivotably coupled to an outer surface of the delivery system to pivotably move with respect to the delivery system, and having a distal region more flexible than a proximal region;
- wherein:
- the elongate tool guide is pivotably movable, with respect to the delivery system, from a deployment configuration to working configuration to access a working site along the delivery system; and
- the more flexible distal region of the elongate tool guide is flexible to assist in moving the elongate tool guide with respect to the delivery system between the deployment configuration and the working configuration.

2. The medical device of claim 1, wherein the lumen extending through the delivery system extends along a delivery system lumen axis.

3. The medical device of claim 2, wherein the elongate tool guide defines a tool lumen extending along a tool lumen axis.

4. The medical device of claim 3, wherein when the elongate tool guide is in the delivery configuration, the tool lumen axis is parallel with the delivery system lumen axis.

5. The medical device of claim 3, wherein when the elongate tool guide is in the working configuration, the tool lumen axis intersects the delivery system lumen axis adjacent the distal end region of the elongate tool guide.

6. The medical device of claim 1, wherein the elongate tool guide body comprises:
- a guide structure adapted to be secured relative to the distal end of the delivery system; and
- a polymeric tubular member secured to the guide structure and extending proximally therefrom.

7. The medical device of claim 6, wherein the guide structure is adapted to be rigidly secured to an intervening structure between the guide structure and a distal end of the delivery system.

8. The medical device of claim 1, wherein the elongate tool guide further includes a guide structure pivotably coupled with respect to the delivery system and adapted to rotate about a pivot point, wherein the elongate tool guide moves, with respect to the delivery system, from its delivery configuration into its working configuration in response to a tool being extended distally through the elongate tool guide to cause the guide structure to rotate about the pivot point.

9. The medical device of claim 1, wherein the elongate tool guide body comprises:
- a guide structure pivotably secured to an intervening structure between the guide structure and the distal end of the delivery system;
- a polymeric tubular member secured to the guide structure and extending proximally therefrom, the guide structure and the polymeric tubular member together defining a lumen; and
- a pivot structure that protrudes into the lumen such that a tool being extended distally through the elongate tool guide will contact the pivot structure, where further distal urging of the tool will cause the tool to interact with the pivot structure and cause the guide structure to pivot relative to the distal assembly to move the elongate tool guide from its delivery configuration into its working configuration.

10. The medical device of claim 1, wherein the elongate tool guide body further comprises:
- a lumen; and
- a metallic ribbon extending through the second lumen, the metallic ribbon movable between a linear configuration in which the metallic ribbon is straight and a remembered configuration in which the metallic ribbon is curved;
- wherein the elongate tool guide is straight when the metallic ribbon is straight and the elongate tool guide is curved when the metallic ribbon is curved.

11. The medical device of claim 1, wherein the elongate tool guide body further comprises:
- a lumen; and
- an elongate bi-stable member extending through the lumen, the elongate bi-stable member movable between a stable configuration in which the elongate bi-stable member is straight and an unstable configuration in which the metallic ribbon is curved;

wherein the elongate tool guide is straight when the bi-stable metal element is straight and the elongate tool guide is curved when the bi-stable metal element is curved.

12. A medical device, comprising:

a delivery system including a delivery lumen extending along a delivery system lumen axis; and an elongate tool guide extending adjacent the delivery system, along an elongate tool guide axis, and pivotably coupled to the delivery system to pivotably move with respect to the delivery system;

wherein:

the elongate tool guide includes an elongate tool guide tubular body defining a tool lumen extending along a tool lumen axis;

the elongate tool guide has having a distal region more flexible than a proximal region;

the elongate tool guide is pivotably movable, with respect to the delivery system, from a delivery configuration to a working configuration to access a working site along the delivery system; and the more flexible distal region of the elongate tool guide is flexible to assist in moving the elongate tool guide with respect to the delivery system between the deployment configuration and the working configuration.

13. The medical device of claim 12, wherein the distal region of the elongate tool guide is pivoted relative to the delivery system and is curved outwardly away from the distal region of the delivery system when in the working configuration.

14. The medical device of claim 12, wherein the elongate tool guide tubular body comprises:

a guide structure fixedly secured to the distal assembly; and a polymeric tubular member secured to the guide structure and extending proximally therefrom.

15. The medical device of claim 12, wherein the elongate tool guide further includes a guide structure pivotably coupled with respect to the delivery system and rotatable about a pivot point, wherein the elongate tool guide moves, with respect to the delivery system, from its delivery configuration into its working configuration in response to a tool being extended distally through the elongate tool guide to cause the guide structure to rotate about the pivot point.

16. The medical device of claim 13, wherein the elongate tool guide body comprises:

a guide structure pivotably secured to the distal assembly;

a polymeric tubular member secured to the guide structure and extending proximally therefrom, the guide structure and the polymeric tubular member together defining a lumen; and a pivot structure that protrudes into the lumen such that a tool being extended distally through the elongate tool guide will contact the pivot structure, where further distal urging of the tool will cause the tool to interact with the pivot structure and cause the guide structure to pivot relative to the distal assembly to move the elongate tool guide from its delivery configuration into its working configuration.

17. The medical device of claim 13, wherein the elongate tool guide body further comprises:

a second lumen; and a metallic ribbon extending through the second lumen, the metallic ribbon movable between a linear configuration in which the metallic ribbon is straight and a remembered configuration in which the metallic ribbon is curved;

wherein the elongate tool guide is straight when the metallic ribbon is straight and the elongate tool guide is curved when the metallic ribbon is curved.

18. The medical device of claim 13, wherein the elongate tool guide body further comprises:

a second lumen; and an elongate bi-stable member extending through the second lumen, the elongate bi-stable member movable between a stable configuration in which the elongate bi-stable member is straight and an unstable configuration in which the metallic ribbon is curved;

wherein the elongate tool guide is straight when the bi-stable metal element is straight and the elongate tool guide is curved when the bi-stable metal element is curved.

19. A medical device, comprising:

an endoscope including a working lumen extending through the endoscope; and an elongate tool guide extending along and pivotably coupled to an outer surface of the endoscope to pivotably move with respect to the endoscope, and having a distal region more flexible than a proximal region;

wherein:

the elongate tool guide is pivotably movable from a deployment configuration to a working configuration to access a working site along the endoscope; and the more flexible distal region of the elongate tool guide is flexible to assist in moving the elongate tool guide with respect to the endoscope between the deployment configuration and the working configuration.

20. The medical device of claim 19, wherein:

the working lumen of the endoscope extends along an endoscope lumen axis; and the elongate tool guide defines a tool lumen extending along a tool lumen axis;

when the elongate tool guide is in the delivery configuration, the tool lumen axis is parallel with the working lumen axis; and when the elongate tool guide is in the working configuration, the tool lumen axis intersects the working lumen axis adjacent the distal end region of the elongate tool guide.

* * * * *